(12) United States Patent
Ollerenshaw et al.

(10) Patent No.: US 11,110,066 B2
(45) Date of Patent: *Sep. 7, 2021

(54) IMPLANTABLE DEVICES FOR DELIVERY OF BIOACTIVE AGENTS

(71) Applicant: Sorrento Therapeutics, Inc., San Diego, CA (US)

(72) Inventors: Jeremy Ollerenshaw, Alpharetta, GA (US); Emily Reichart, Milford, OH (US); Russell F. Ross, Atlanta, GA (US)

(73) Assignee: SORRENTO THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/354,223

(22) PCT Filed: Oct. 16, 2012

(86) PCT No.: PCT/IB2012/055622
§ 371 (c)(1),
(2) Date: Apr. 25, 2014

(87) PCT Pub. No.: WO2013/061209
PCT Pub. Date: May 2, 2013

(65) Prior Publication Data
US 2014/0287019 A1 Sep. 25, 2014

Related U.S. Application Data

(60) Provisional application No. 61/552,059, filed on Oct. 27, 2011.

(51) Int. Cl.
| | |
|---|---|
| *A61K 9/70* | (2006.01) |
| *A61K 9/00* | (2006.01) |
| *A61L 27/54* | (2006.01) |
| *A61M 37/00* | (2006.01) |
| *A61L 31/16* | (2006.01) |
| *A61L 31/14* | (2006.01) |
| *A61L 27/50* | (2006.01) |
| *A61F 2/82* | (2013.01) |
| *A61F 2/00* | (2006.01) |

(52) U.S. Cl.
CPC .......... *A61K 9/7007* (2013.01); *A61K 9/0024* (2013.01); *A61K 9/0097* (2013.01); *A61L 27/50* (2013.01); *A61L 27/54* (2013.01); *A61L 31/14* (2013.01); *A61L 31/16* (2013.01); *A61M 37/0015* (2013.01); *A61F 2/82* (2013.01); *A61F 2002/0081* (2013.01); *A61F 2250/0067* (2013.01); *A61L 2400/12* (2013.01); *A61L 2400/18* (2013.01); *A61M 2037/0053* (2013.01)

(58) Field of Classification Search
CPC .. A61K 9/7007; A61K 9/0024; A61K 9/0097; A61L 27/50; A61L 27/54; A61L 31/14; A61L 2400/12; A61L 2400/18; A61L 31/16; A61M 2037/0053; A61M 37/0015
See application file for complete search history.

(56) References Cited

U.S. PATENT DOCUMENTS

| | | | |
|---|---|---|---|
| 3,964,482 | A | 6/1976 | Gerstel et al. |
| 4,051,840 | A | 10/1977 | Kantrowitz et al. |
| 4,698,062 | A | 10/1987 | Gale et al. |
| 6,132,755 | A | 10/2000 | Eicher et al. |
| 6,334,856 | B1 | 1/2002 | Allen et al. |
| 6,471,993 | B1 * | 10/2002 | Shastri et al. ............... 424/486 |
| 6,611,707 | B1 | 8/2003 | Prausnitz et al. |
| 6,656,147 | B1 | 12/2003 | Gerstek et al. |
| 6,663,820 | B2 | 12/2003 | Arias et al. |
| 6,767,341 | B2 | 7/2004 | Cho |
| 6,881,203 | B2 | 4/2005 | Delmore et al. |
| 6,923,930 | B2 | 8/2005 | Ling et al. |
| 6,926,953 | B2 | 8/2005 | Nealey et al. |
| 6,979,347 | B1 | 12/2005 | Wu et al. |
| 6,995,336 | B2 | 2/2006 | Hunt et al. |
| 7,022,465 | B2 | 4/2006 | Heidari |
| 7,041,228 | B2 | 5/2006 | Heidari |

(Continued)

FOREIGN PATENT DOCUMENTS

| | | |
|---|---|---|
| EP | 2 100 850 | 9/2009 |
| EP | 2100850 A1 | 9/2009 |

(Continued)

OTHER PUBLICATIONS

Biggs, Manus J. P., et al., Wiley Periodicals, Inc. J Biomed Mater Res 91A (2009) pp. 195-208.*
Abstract of Japanese Patent—JP2008237673, Oct. 9 2008, 1 page.
Abstract of Japanese Patent—JP2009207733, Sep. 17, 2009, 1 page.
Abstract of Japanese Patent—JPH08337521, Dec. 24, 1996, 2 pages.
Inkyu Park et al., Towards the silicon nanowire-based sensor for intracellular biochemical detection, 6 pages, Apr. 1, 2007, Biosensors and Bioelectronics, vol. 22, No. 9-10.

(Continued)

*Primary Examiner* — Andrew S Rosenthal
*Assistant Examiner* — Lyndsey M Beckhardt
(74) *Attorney, Agent, or Firm* — Armstrong Teasdale LLP

(57) ABSTRACT

An implantable delivery device and method for utilizing the device to delivery a bioactive agent to a subject in need thereof is described. The device includes a pattern of structures fabricated on a surface of the device to form a nanotopography. A random or non-random pattern of structures may be fabricated such as a complex pattern including structures of differing sizes and/or shapes. The device may be located adjacent tissue such as an endovascular implant or a perivascular implant, and may deliver the bioactive agent without triggering an immune or foreign body response to the bioactive agent.

20 Claims, 12 Drawing Sheets

(56) References Cited

U.S. PATENT DOCUMENTS

| | | |
|---|---|---|
| 7,108,681 B2 | 9/2006 | Gartstein et al. |
| 7,115,108 B2 | 10/2006 | Wilkinson et al. |
| 7,129,554 B2 | 10/2006 | Lieber et al. |
| 7,131,987 B2 | 11/2006 | Sherman et al. |
| 7,137,336 B2 | 11/2006 | Heidari et al. |
| 7,185,663 B2 | 3/2007 | Koch et al. |
| 7,189,435 B2 | 3/2007 | Tuominen et al. |
| 7,195,734 B2 | 3/2007 | Heidari |
| 7,252,492 B2 | 8/2007 | Olsson et al. |
| 7,315,758 B2 | 1/2008 | Kwiatkowski et al. |
| 7,332,339 B2 | 2/2008 | Canham |
| 7,364,568 B2 | 4/2008 | Angel et al. |
| 7,374,864 B2 | 5/2008 | Guo et al. |
| 7,416,541 B2 | 8/2008 | Yuzhakov et al. |
| 7,429,258 B2 | 9/2008 | Angel et al. |
| 7,473,244 B2 | 1/2009 | Frazier et al. |
| 7,537,590 B2 | 5/2009 | Santini, Jr. et al. |
| 7,572,405 B2 | 8/2009 | Sherman et al. |
| 7,578,954 B2 | 8/2009 | Gartstein et al. |
| 7,611,481 B2 | 11/2009 | Cleary et al. |
| 7,658,728 B2 | 2/2010 | Yuzhakov |
| 7,670,127 B2 | 3/2010 | Heidari |
| 7,687,007 B2 | 3/2010 | Ling et al. |
| 7,704,425 B2 | 4/2010 | Heidari et al. |
| 7,717,693 B2 | 5/2010 | Keil et al. |
| 7,754,131 B2 | 7/2010 | Olsson et al. |
| 7,803,574 B2 | 9/2010 | Desai et al. |
| 7,828,827 B2 | 11/2010 | Gartstein et al. |
| 7,846,488 B2 | 12/2010 | Johnson et al. |
| 7,855,046 B2 | 12/2010 | Suleski |
| 7,862,849 B2 | 1/2011 | Stellacci et al. |
| 7,914,480 B2 | 3/2011 | Cleary et al. |
| 7,914,813 B2 | 3/2011 | Adachi et al. |
| 7,981,346 B2 | 7/2011 | Griss et al. |
| 8,052,633 B2 | 11/2011 | Kendall |
| 8,118,753 B2 | 2/2012 | Cho et al. |
| 8,137,736 B2 | 3/2012 | Zhu et al. |
| 8,238,995 B2 | 8/2012 | Chandrasekaran et al. |
| 8,366,677 B2 | 2/2013 | Kaspar et al. |
| 8,389,205 B2 | 3/2013 | Duerig et al. |
| 8,419,708 B2 | 4/2013 | Tokumoto et al. |
| 8,506,530 B2 | 8/2013 | Laermer et al. |
| 8,551,391 B2 | 10/2013 | Chang et al. |
| 8,696,637 B2 | 4/2014 | Ross |
| 8,944,804 B2 | 2/2015 | Robeson et al. |
| 2002/0133129 A1 | 9/2002 | Arias et al. |
| 2002/0183688 A1 | 12/2002 | Lastovich et al. |
| 2004/0028875 A1 | 2/2004 | Van Rijn et al. |
| 2004/0063100 A1 | 4/2004 | Wang |
| 2004/0087992 A1 | 5/2004 | Gartstein et al. |
| 2004/0106904 A1 | 6/2004 | Gonnelli et al. |
| 2005/0112636 A1 | 5/2005 | Hurt et al. |
| 2005/0119723 A1* | 6/2005 | Peacock, III ............... 623/1.15 |
| 2005/0124967 A1 | 6/2005 | Kaestner et al. |
| 2005/0137531 A1 | 6/2005 | Prausnitz et al. |
| 2005/0203613 A1* | 9/2005 | Arney ................ A61F 2/92 |
| | | 623/1.42 |
| 2006/0024358 A1 | 2/2006 | Santini, Jr. et al. |
| 2006/0051404 A1 | 3/2006 | Yeshurun et al. |
| 2006/0204738 A1 | 9/2006 | Dubrow et al. |
| 2007/0066934 A1 | 3/2007 | Etheredge, III et al. |
| 2007/0078376 A1 | 4/2007 | Smith |
| 2007/0081977 A1 | 4/2007 | Horstmann |
| 2007/0088248 A1 | 4/2007 | Glenn et al. |
| 2007/0112309 A1 | 5/2007 | Zucker |
| 2007/0112548 A1 | 5/2007 | Dickerson et al. |
| 2007/0249552 A1 | 10/2007 | Khalili et al. |
| 2007/0250018 A1 | 10/2007 | Adachi et al. |
| 2008/0051699 A1 | 2/2008 | Choi et al. |
| 2008/0097352 A1 | 4/2008 | Beck et al. |
| 2008/0108958 A1 | 5/2008 | Carter et al. |
| 2008/0139911 A1* | 6/2008 | Chandrasekaran .. A61B 5/0408 |
| | | 600/382 |
| 2008/0195035 A1 | 8/2008 | Frederickson et al. |
| 2008/0200883 A1* | 8/2008 | Tomono ............ A61M 37/0015 |
| | | 604/272 |
| 2008/0214916 A1* | 9/2008 | Yodfat ............... A61B 5/14532 |
| | | 600/347 |
| 2008/0217180 A1 | 9/2008 | Doye et al. |
| 2008/0269666 A1* | 10/2008 | Wang ................... A61B 17/205 |
| | | 604/21 |
| 2008/0269685 A1 | 10/2008 | Singh et al. |
| 2008/0305989 A1 | 12/2008 | Wen et al. |
| 2008/0311172 A1 | 12/2008 | Schapira et al. |
| 2008/0312610 A1 | 12/2008 | Binks et al. |
| 2009/0012494 A1 | 1/2009 | Yeshurun et al. |
| 2009/0093871 A1* | 4/2009 | Rea et al. ..................... 623/1.11 |
| 2009/0093879 A1 | 4/2009 | Wawro et al. |
| 2009/0099502 A1 | 4/2009 | Tokumoto et al. |
| 2009/0118662 A1 | 5/2009 | Schnall |
| 2009/0137926 A1 | 5/2009 | Srinivasan et al. |
| 2009/0177273 A1* | 7/2009 | Piveteau et al. ............. 623/1.46 |
| 2009/0232870 A1 | 9/2009 | Srivastava et al. |
| 2010/0021464 A1 | 1/2010 | Archambeau et al. |
| 2010/0076035 A1 | 3/2010 | Carter et al. |
| 2010/0119557 A1 | 5/2010 | Boyden et al. |
| 2010/0121307 A1 | 5/2010 | Lockard et al. |
| 2010/0168506 A1 | 7/2010 | Moon et al. |
| 2010/0215580 A1 | 8/2010 | Hanes et al. |
| 2010/0274203 A1 | 10/2010 | Lee et al. |
| 2011/0046557 A1 | 2/2011 | Lee et al. |
| 2011/0059150 A1 | 3/2011 | Kendall et al. |
| 2011/0144591 A1 | 6/2011 | Ross |
| 2011/0270221 A1 | 11/2011 | Ross |
| 2012/0089117 A1 | 4/2012 | Junginger et al. |
| 2012/0109065 A1 | 5/2012 | Backes |
| 2012/0128932 A1 | 5/2012 | Veith et al. |
| 2013/0144217 A1 | 6/2013 | Ross |
| 2013/0144257 A1 | 6/2013 | Ross |
| 2013/0158505 A1 | 6/2013 | Ross |
| 2013/0165861 A1 | 6/2013 | Ross |
| 2013/0211310 A1 | 8/2013 | Bommarito et al. |
| 2013/0331792 A1 | 12/2013 | Karp et al. |

FOREIGN PATENT DOCUMENTS

| | | |
|---|---|---|
| WO | WO 99/45860 | 9/1999 |
| WO | 2011/116388 A1 | 9/2001 |
| WO | 01/75164 A2 | 10/2001 |
| WO | 02/30506 A2 | 4/2002 |
| WO | 02/32480 A2 | 4/2002 |
| WO | 03/020359 A2 | 3/2003 |
| WO | 03/024508 A2 | 3/2003 |
| WO | WO 03/092785 A1 | 11/2003 |
| WO | 2005/049128 | 6/2005 |
| WO | 2005/049128 A1 | 6/2005 |
| WO | 2006/062974 | 6/2006 |
| WO | 2006/062974 A2 | 6/2006 |
| WO | 2006/075689 A1 | 7/2006 |
| WO | 2007/012114 | 2/2007 |
| WO | 2007/012114 A1 | 2/2007 |
| WO | 2007/081876 | 7/2007 |
| WO | 2007/112309 A2 | 10/2007 |
| WO | 2008/003564 | 1/2008 |
| WO | 2008/003564 A1 | 1/2008 |
| WO | 2008/024141 | 2/2008 |
| WO | 2008/024141 A2 | 2/2008 |
| WO | 2008/115883 | 9/2008 |
| WO | WO 2008/115883 * | 9/2008 |
| WO | 2009/079589 | 6/2009 |
| WO | 2009/079589 A2 | 6/2009 |
| WO | 2009/113856 | 9/2009 |
| WO | 2010/070628 A1 | 6/2010 |
| WO | WO 2010/062919 A1 | 6/2010 |
| WO | WO 2010/126640 A2 | 11/2010 |
| WO | WO-2011012213 A2 * | 2/2011 ........... A61L 27/047 |
| WO | 2011/135531 | 11/2011 |
| WO | 2011/135531 A2 | 11/2011 |
| WO | 2012/046149 A1 | 4/2012 |

OTHER PUBLICATIONS

International Search Report and Written Opinion for PCT/IB2012/055622 dated Feb. 28, 2013, 13 pages.

(56) References Cited

OTHER PUBLICATIONS

Ainslie et al., "Microfabricated implants for application in therapeutic delivery, tissue engineering, and biosensing." Royal Society of Chemistry. 8. (2008): 1864-1878.
Ainslie et al., "Microfabricated Devices for Enhanced Bioadhesive Drug Delivery: Attachment to and Small-Molecule Release Throug a Cell Monolayer Under Flow." Small. (2009).
Bekarde, Iil Gercek. "Biomimetic Apatite-coated PCL Scaffolds: Effect of Surface Nanotopography on Cellular Functions." Journal of Bioactive and Compatible Polymers . 24.6 (2009): 507-524.
Berry et al., "The interaction of human bone marrow cells with nanotopographical features in three dimensional constructs." Journal of Biomedical Materials Research Part A. 79A.2 (2006): 431-439.
Biehl et al., "Proliferation of Mouse Embryonic Stem Cell Progeny and the Spontaneous Contractile Activity of Cardiomyocytes Are Affected by Microtopography," Developmental Dynamics . 238. (2009): 1964-1973.
Chandler, David L . . . "PhysOrg.com." Harnessing nanopatterns; Tiny textures can produce big differences. N.p., Sep. 24, 2009. Web. Dec. 1, 2009. <http://www.physorg.com/news173004362.html>.
Choi et al. "Cell interaction with three-dimensional sharp-tip nanotopography." Biomaterials. 28.9 (2007): 1672-1679.
Chun et al., "The role of polymer nanosurcace roughness and the submicron pores in improving bladder urothelial cell density and inhibiting calcium oxalate stone formation." Nanotechnology. 20.8 (2009): 85104.
Cohn, Abby. "Drug Delivery, Nanoscale." Innovations. (2009).
Curtis et al., "Cell signaling arising from nanotopography: implicatinos for nanomedicaldevices." Nanomedicine. 1.1 (2006): 67-72.
Dalby et al., "Increasing Fibroblast Response to Materials Using Nanotopography: Morphological and Genetic measurements of Cell Response to 13-nm-High Polymer Demixed Islands." Experimental Cell Research. 276.1 (2002): 1-9.
Dalby et al., "Nano-Topography Induces Mechanotransduction in Human Fibroblasts." European Cells and Materials . 6.2 (2003): 31.
Dalby et al., "Attempted endocytosis of nano-environment produced by colloidal lithography by human fibroblasts." Expeental Cell Research. 295. (2004): 387-394.
Dalby, Matthew Jr. "Nanostructured surfaces: cell engineering and cell biology." Nanomedicine. 4.3 (2009): 247-248.
Fischer et al., "Biomimetic Nanowire Coatings for Next Generation Adhesive Drug Delivery Systems." Nano Letters. 9.2 (2009): 716-720.
Hart et al., "Filapodial Sensing of Nanotopography in Osteoprogenitor Cells." European Cells and Materials . 10.2 (2005): 65.
He, et al., "The anatase phase of nanotopography titania plays an important role on osteoblast cell morphology and proliferation", Journal of Mater. Sci: Mater Med (2008), 19;3465-3472.
Hu et al., "Surface Energy Induced Patterning of Polymer Nanostructures for Cancer Diagnosis and Therapy." IEEE Nano 2007 Conference Paper. (2007).
Lim et al., "Human foetal osteoblastic cell response to polymer-demixed nanotopographic interfaces." Journal of the Royal Society Interface. 2.2 (2005): 97-108.
Mahdavi et al., "A biodegradable and biocompatible gecko-inspired tissue adhesive." PNAS. 105.7 (2008): 2307-2312.
Meirelles et al., "The effect of chemical and nanotopographical modifications on the early stages of osseointegration." International Journal of Oral and Maxillofacial Implants. 23.4 (2008): 641-647.
Ng et al., "Study of substrate topographical effects on epithelial cell behavior using etched alpha-particle tracks on PADC films." Nuclear Instruments and Methods in Physics Research Section B: Beam Interactions with Materials and Atoms. 266.14 (2008): 3247-3256.
Peng et al., "The effect of $TiO_2$ nanotubes on endothelial function and smooth muscle proliferation." Journal of Biomaterials. 30. (2009): 1268-1272.
Peng et al., "Long-Term Small Molecule and Protein Elution from $TiO_2$ Nanotubes." Nano Letters. 9.5 (2009): 1932-1936.
Teo et al. "The effect of micro and nanotopography on endocytosis in drug and gene delivery systems", Biomaterials, 32 (2011), 9866-9875.
Thakar et al., "Contractility-Dependent Modulation of Cell Proliferation and Adhesion by Microscale Topographical Cues." Small. 4.9 (2008): 1416-1424.
Wang et al., "Nano patterned PDMS for periodontal ligament fibroblast culture." Surface and Coatings Technology. 204.4 (2009): 525-530.
Wei et al., "Protein adsorption on materials surfaces with nanotopography." Chinese Science Bulletin. 52.23 (2007): 3169-3173.
Wood, M.A. "Colloidal lithography and current fabrication techniques producing in-plane nanotopography for biological applications." Journal of the Royal Society Interface. 4.12 (2007): 1:17.
Yao et al., "Nano-Surface Modification on Titanium Implants for Drug Delivery." Materials Research Society . (2007).
Yim et al., "Nanopattern-induced changes in morphology and motility of smooth muscle cells," Journal of Biomaterials. 58.1 (2005).
EP Extended Search Report for related application 19170819.7 dated Jul. 23, 2019; 11 pp.
EPO Examination Report for EP Patent Application 19170819.7 dated Jul. 23, 2020; 5 pp.

\* cited by examiner

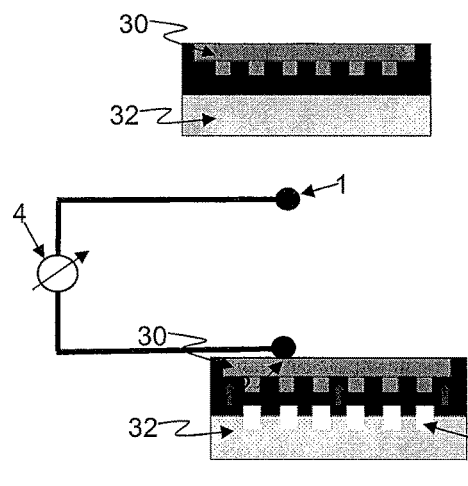
FIG. 8A
FIG. 8B
FIG. 8C
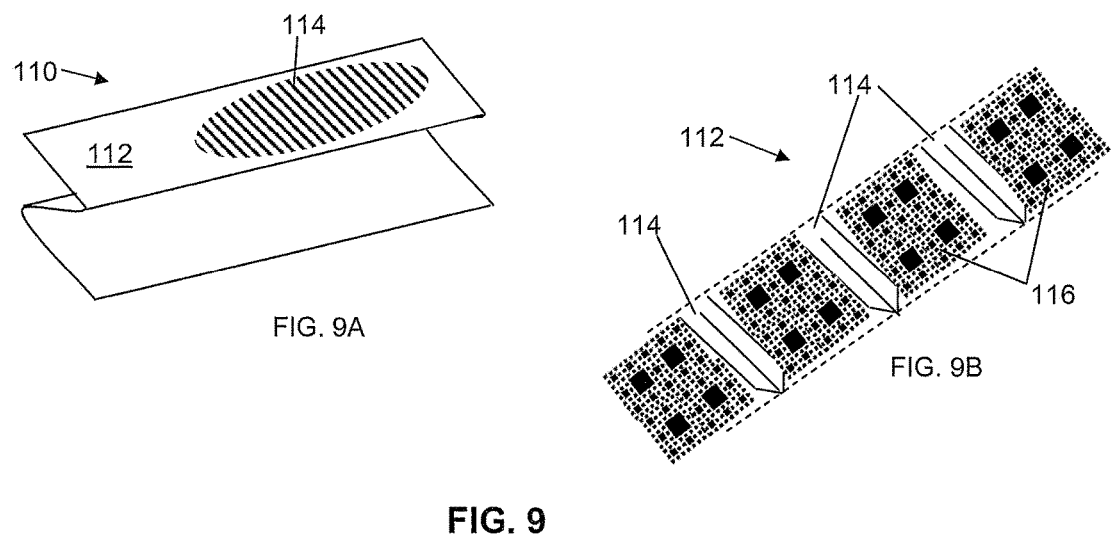
FIG. 9A
FIG. 9B
FIG. 9

DN1

Hole depth = 500nm

DN2

Hole depth = 500nm

DN3

Hole Depth = 500 nm

DN4

Hole depth = 400-500nm (Random Variation)

FIG. 10E
NTTAT2
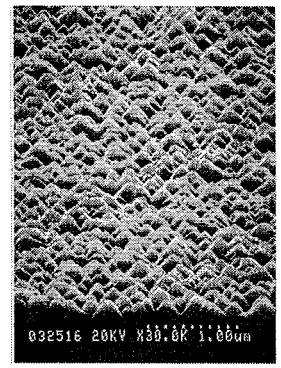
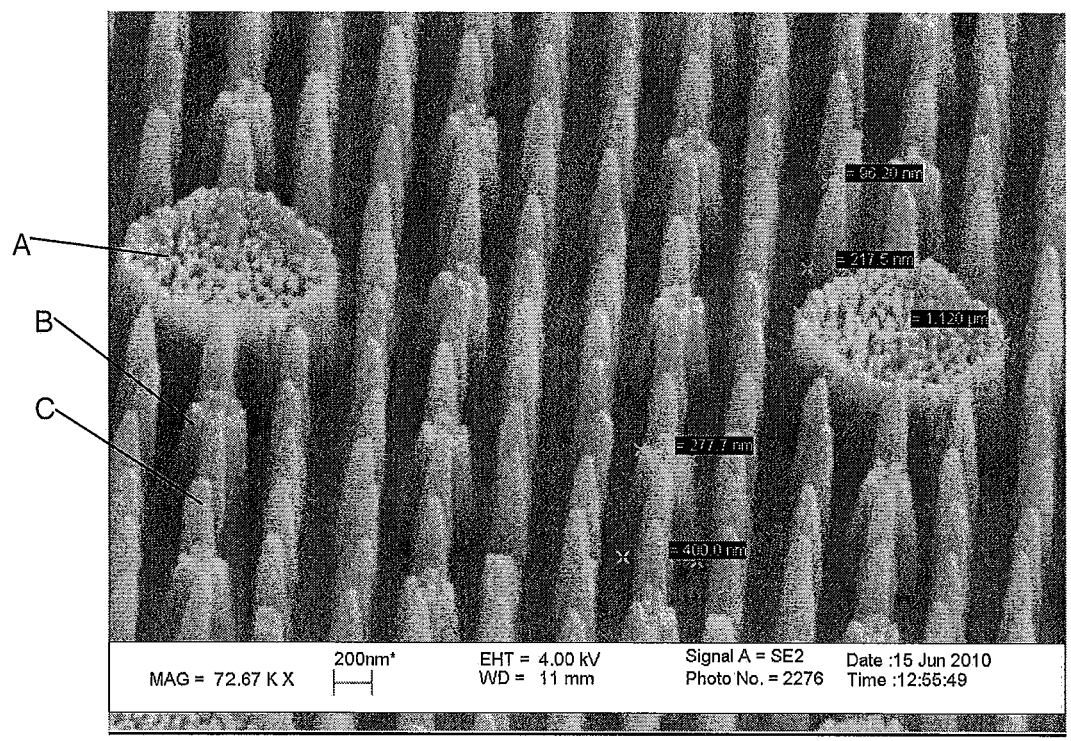
FIG. 11

IMPLANTABLE DEVICES FOR DELIVERY OF BIOACTIVE AGENTS

CROSS REFERENCE TO RELATED APPLICATIONS

The present application is the U.S. national filing of International Patent Application Number PCT/IB2012/055622 having a filing date of Oct. 16, 2012, which claims filing benefit of U.S. Provisional Patent Application Ser. No. 61/552,059 having a filing date of Oct. 27, 2011, both of which are incorporated herein by reference in their entirety.

BACKGROUND

Implantable devices that provide for targeted delivery of a bioactive agent (e.g., a drug or a therapeutic) to a targeted area in an active state and at effective concentrations are a long sought goal. Many difficulties must be overcome to reach this goal. For instance, a device must be implantable at the desired site with minimal disruption to the local area, and the bioactive agent must be released from the device in such a fashion so as to successfully cross any natural boundaries while avoiding detection and destruction by the body's own defense systems.

Implantable devices such as endovascular and perivascular implants have been found useful for providing bioactive agents to a subject's system. Unfortunately, the presence of such implants often leads to local inflammation, which can instigate an immune response by the subject's system that targets the bioactive agent for destruction and prevents delivery. In addition, natural boundaries such as vessel walls, the pericardial sac, and other natural barriers can prevent delivery of a bioactive agent across the barrier to the targeted tissue.

What are needed in the art are devices and methods for delivery of bioactive agents. More specifically, what are needed are implantable devices and methods that can successfully deliver a bioactive agent and can also prevent targeting of the bioactive agent by the body's own defensive mechanisms.

SUMMARY

According to one embodiment, disclosed is an implantable delivery device for delivery of a bioactive agent to a subject. The device can include a plurality of nanostructures fabricated on a surface of the implantable delivery device, the nanostructures being arranged in a predetermined pattern. In addition, the device can include a bioactive agent within or on the implantable delivery device.

Also disclosed is a method for forming an implantable delivery device, the method including fabricating a pattern of nanostructures on a surface of the implantable delivery device.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIGS. 8A-8C schematically illustrate a nanoimprinting method as may be utilized in one embodiment in forming a device.

FIG. 9A illustrates one embodiment of an implantable device as described herein.

FIG. 9B illustrates a section of the device of FIG. 9A.

FIGS. 10A-10E illustrate several nanotopography patterns as described herein.

FIG. 11 is an SEM of a film including a nanopatterned surface.

DETAILED DESCRIPTION OF REPRESENTATIVE EMBODIMENTS

Figure 1A:
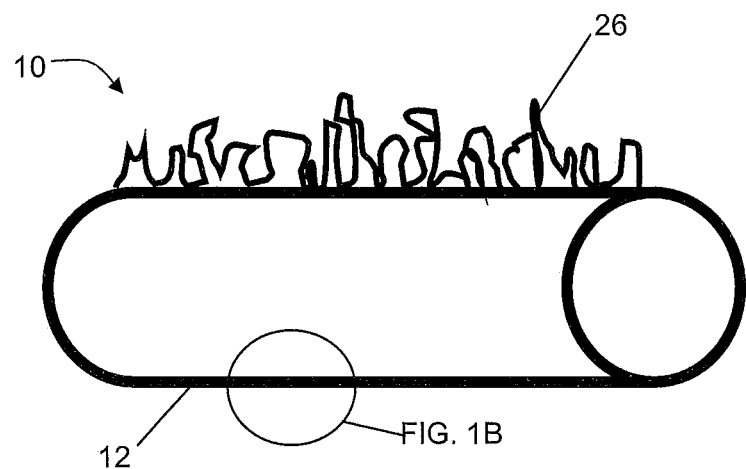
FIG. 1A illustrates one embodiment of an implantable device as described herein.

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

Implantable deliver devices are described as are methods that provide a route for delivering a bioactive agent internally to a subject by use of the implantable delivery devices. More specifically, the implantable delivery devices include a pattern of structures fabricated on a surface, at least a portion of which are fabricated on a nanometer scale. The implantable delivery device also contains a bioactive agent within or on a surface of the device for delivery from the device to a subject in need thereof. Implantable delivery devices can include patches, stents, slings, and the like that can be loaded with a bioactive agent for internal delivery to a subject.

As utilized herein, the term 'fabricated' generally refers to a structure that has been specifically designed, engineered, and/or constructed so as to exist at a surface of the implantable delivery device and is not to be equated with a surface feature that is merely an incidental product of the device formation process. Thus, there will be a predetermined pattern of nanostructures on a surface of the implantable delivery device.

Subjects as may benefit from the methods and devices can include any animal subject in need of delivery of a bioactive agent. For instance a subject can be a human or any other mammal or animal as may benefit from internal delivery of bioactive agents.

The implantable delivery device may be constructed from a variety of materials, including metals, ceramics, semiconductors, organics, polymers, etc., as well as composites thereof. By way of example, pharmaceutical grade stainless steel, titanium, nickel, iron, gold, tin, chromium, copper, alloys of these or other metals, silicon, silicon dioxide, and polymers may be utilized. The implantable delivery device is formed of a biocompatible, implantable material that is capable of carrying a pattern of structures as described herein on a surface. The term "biocompatible" generally refers to a material that does not substantially adversely affect the cells or tissues in the area where the implantable delivery device is to be located. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid, polylactide, polyglycolide, polylactide-co-glycolide, copolymers with polyethylene glycol, polyanhydrides, poly(ortho)esters, polyurethanes, poly(butyric acid), poly(valeric acid), and poly(lactide-co-caprolactone). Other suitable materials may include, without limitation, polycarbonate, polymethacrylic acid, ethylenevinyl acetate, polytetrafluoroethylene, and polyesters. The implantable delivery device (or portions thereof) may be non-porous or porous in nature, may be homogeneous or heterogeneous across the device with regard to materials, geometry, solidity, and so forth, and may have a rigid fixed or a semi-fixed shape.

Regardless of the materials employed, the implantable delivery device may be used for interaction with tissue, such as in delivery of a bioactive agent to a blood vessel, e.g., the vessel lumen, to the digestive tract, or to an organ. For example, the implantable device may be used to deliver an agent to the organ tissue or to one or more cell types of the tissue, for structural support of a tissue, and so forth. The implantable device may be used in one embodiment for transport of a substance across one or more layers of a barrier, for instance a vessel wall. During use, the device may interact with surrounding biological components and regulate or modulate (i.e., change) intracellular and/or intercellular signal transduction associated with cell/cell interactions, endocytosis, inflammatory response, and so forth.

The implantable delivery device may be utilized for internal delivery of agents without instigating a foreign body or immune response. More specifically, and without wishing to be bound by any particular theory, it is believed that through interaction between the nanotopography on a surface of the device and surrounding biological materials or structures, the implantable delivery device as well as the bioactive agent delivered by the device may avoid being targeted by the body's defense mechanisms. As such, the implantable devices can elute biological agent for a longer period of time as compared to previously known implantable devices that become inactive or must be removed soon after implant, due to the body's natural defense mechanisms being raised against the device. The implantable devices described herein can provide for longer dosing, for example active elution over a period of weeks or months, such as for about 12 months, in one embodiment, due to avoidance of any foreign body response.

When a foreign body is implanted at a site and is recognized as foreign, extracellular matrix material and/or plasma proteins can aggregate to the foreign body. Depending upon the specific materials that aggregate to the foreign body, these materials can instigate various reactions including containment of the foreign body and/or neutralization of the foreign body. For instance, when a delivery device, e.g., an endovascular stent, is held in contact with a vessel wall and is recognized as a foreign body, certain defense responses will ensue.

One of the initial responses upon recognition of an implant as a foreign body is inflammation. A consequence of inflammation is increased recruitment of immune cells and related extracellular materials to the local site. These materials can include proteins that can mark both the implant as well as any other bodies in the area, e.g., a molecular body associated with the primary instigator of the response, as a foreign body. Accordingly, when the implant is recognized as a foreign body, a cascade of initial responses ensues. Among these initial responses are those that can instigate a second response directed against the bioactive agent delivered by the implant.

Natural defense mechanisms directed against a bioactive agent delivered by an implantable delivery device can include binding of proteins to the bioactive agent, thereby marking it as a foreign particle. When these marked particles travel through the subject's system, for instance through the spleen or the liver, they can be marked for destruction and/or removal, such as via hepatic clearance. Thus, the recognition of an implantable device as a foreign body can also lead to recognition of a delivered bioactive agent as a foreign body and accumulation of the bioactive agent in the spleen as well as in the liver, both of which filter and remove pathogens from the subject's system.

FIG. 1A illustrates a typical implantable delivery device 10, in this case a hollow device that may be utilized as, e.g., an endovascular stent. The wall 12 of device 10 may be solid, porous, or may include one or more reservoirs for containment of a bioactive agent to be delivered by use the device 10.

Figure 2:
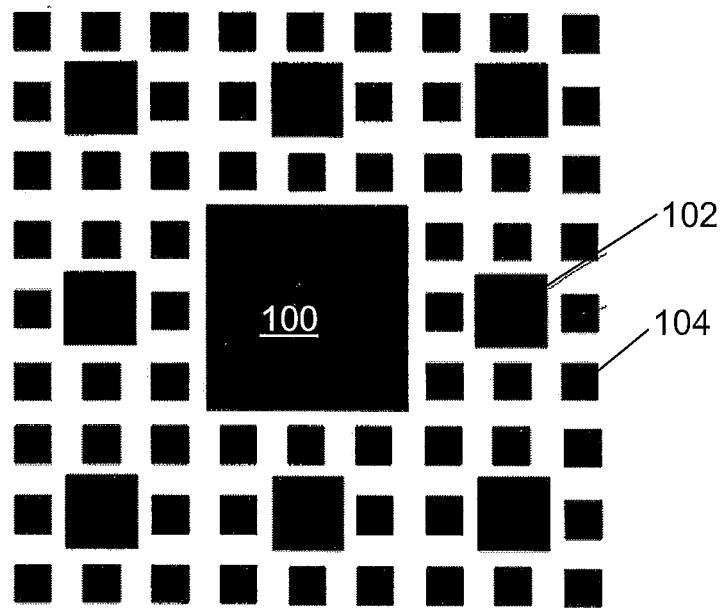
FIG. 2 illustrates one embodiment of a complex pattern that may be formed on a device surface.

FIG. 2 illustrates a portion of the device 10. As can be seen, device 10 includes a reservoir 11 between an outer wall 12a and an inner wall 12b and a channel 16, e.g., an annular bore that may be utilized for, e.g., delivery of an agent from the reservoir 11 to an external location on the device 10. For instance, a channel 16 may allow the passage of a bioactive agent through the channel 16 and into the lumen of a blood vessel.

The dimensions of the channel 16, when present, can be specifically selected to induce capillary flow of a composition including a bioactive agent. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the device, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the wall thickness of the channel 16. The wall thicknesses and the overall size of the reservoir 11 and the inner wall 12*b* that defines the channel 16 may vary to accommodate different volumes, flow rates, and dwell times for the bioactive agent. For example, the thickness of the inner wall 12*b* may be from about 10 micrometers to about 800 micrometers, in some embodiments from about 50 micrometers to about 500 micrometers, and in some embodiments, from about 100 micrometers to about 300 micrometers. The cross-sectional area of the channel 16 may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (inner wall thickness/cross-sectional dimension) of the channel may range from about 1 to about 50, in some embodiments from about 5 to about 40, and in some embodiments from about 10 to about 20. In cases where the cross-sectional dimension (e.g., width, diameter, etc.) and/or inner wall thickness vary as a function of inner wall thickness, the aspect ratio can be determined from the average dimensions.

It should also be understood that the number of channels providing an outlet from a reservoir to a surface of an implantable delivery device can vary. The actual number of channels used in an implantable delivery device may, for example, range from about 500 to about 10,000, in some embodiments from about 2,000 to about 8,000, and in some embodiments, from about 4,000 to about 6,000.

The wall 12 may be constructed from rigid or flexible materials including, without limitation, metal, ceramic, plastic or other material. In addition, the outer wall 12*a* and inner wall 12*b* can be formed of the same or different materials, and an implantable delivery device can include a single reservoir 11 or a plurality of reservoirs throughout the device 10. In addition, a single reservoir can be of any suitable size and shape, for instance within a portion of a device wall 12 or within substantially all of a device wall 12. The wall 12, whether solid in cross section or including an inner wall, outer wall, and reservoir therebetween, can vary in thickness to meet the needs of the device, such as about 1000 micrometers or less, in some embodiments from about 1 to about 500 micrometers, and in some embodiments, from about 10 to about 200 micrometers.

Figure 1B:
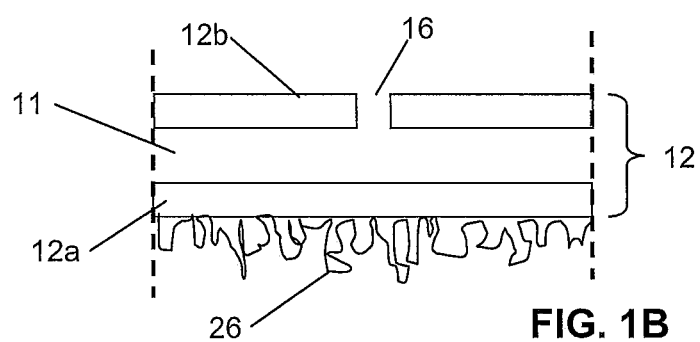
FIG. 1B illustrates a section of the device of FIG. 1A

A surface of device 10 may include a plurality of fabricated structures that define a nanotopography thereon in a random or organized pattern. FIGS. 1A and 1B schematically illustrates a nanotopography 26 defined on the surface of outer wall 12*a* of the device 10. In this particular embodiment, the nanotopography 26 defines a random pattern on the external surface of the device 10. However, the surface(s) of the device upon which the nanotopography is formed on a device is not limited in any way. For instance, a device can include a plurality of fabricated structures one, two or all surfaces of the device, or may include a plurality of fabricated structures on only a portion of a surface. For instance, in the embodiment illustrated in FIG. 1, in which an endovascular stent is illustrated, the nanotopography 26 is fabricated on the outer surface of the device that will be in contact with the vessel wall upon implantation. In this embodiment, the inner surface of the device, i.e., that surface that will face the vessel lumen upon implantation, may also include a fabricated nanotopography thereon. Alternatively, only the inner surface of an endovascular stent may include a nanotopography defined thereon.

In the case of a perivascular stent (an example of which is illustrated in FIG. 9), the nanotopography can be fabricated on the inner surface of the device, as that surface will be the device surface in contact with the vessel wall to which the device can be attached. However, the fabricated nanotopography can also or alternatively be located on the external surface of a perivascular stent, which will face the environment external to the vessel.

In general, an implantable delivery device can include the plurality of fabricated structures at least upon that surface of the device that will be placed against a subject's tissue upon implantation. In addition, it should be understood that delivery of a bioactive agent can be at the surface of the device that includes the plurality of fabricated structures or can be at a different location on the device, for instance at the interior surface of an endovascular stent, as shown in FIG. 1, or at the interior surface of a perivascular stent, as shown in FIG. 9, which could be utilized to deliver the bioactive agent through the vessel wall and to the blood vessel lumen.

An implantable delivery device may include a plurality of identical structures formed on a surface or may include different structures formed of various, sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, structures may vary with regard to size and/or shape and may form a complex nanotopography. For example, a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal.

For instance, it may be regular and relatively easily described in traditional Euclidean geometric language, whereas a fractal may not.

An implantable delivery device surface defining a complex nanotopography may include structures of the same general shape (e.g., pillars) and the pillars may be formed to different scales of measurement (e.g., nano-scale pillars as well as micro-scale pillars). In another embodiment, a device may include at a surface structures that vary in both scale size and shape or that vary only in shape while formed to the same nano-sized scale. Additionally, structures may be formed in an organized array or in a random distribution. In general, at least a portion of the structures may be nanostructures formed on a nano-sized scale, e.g., defining a cross-sectional dimension of less than about 500 nanometers, for instance less than about 400 nanometers, less than about 250 nanometers, or less than about 100 nanometers. The cross sectional dimension of the nanostructures can generally be greater than about 5 nanometers, for instance greater than about 10 nanometers, or greater than about 20 nanometers. For example, the nanostructures can define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

FIG. 2 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes can include larger structures having a cross-sectional dimension formed on a larger scale, e.g., microstructures having a cross-sectional dimension greater than about 500 nanometers in combination with smaller nanostructures. In one embodiment, microstructures of a complex nanotopography can have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 4 can include micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 2 can have a cross-sectional dimension of about 400 nanometers, and pillars 104 can have a cross-sectional dimension of about 200 nanometers.

A nanotopography can be formed of any number of different elements. For instance, a pattern of elements can include two different elements, three different elements, an example of which is illustrated in FIG. 2, four different elements, or more. The relative proportions of the recurrence of each different element can also vary. In one embodiment, the smallest elements of a pattern will be present in larger numbers than the larger elements. For instance in the pattern of FIG. 2, there are eight pillars 104 for each pillar 102, and there are eight pillars 102 for the central large pillar 100. As elements increase in size, there can generally be fewer recurrences of the element in the nanotopography. By way of example, a first element that is about 0.5 times, for instance between about 0.3 times and about 0.7 times in cross-sectional dimension as a second, larger element can be present in the topography about five times or more than the second element. A first element that is approximately 0.25 times, or between about 0.15 times and about 0.3 times in cross-sectional dimension as a second, larger element can be present in the topography about 10 times or more than the second element.

The spacing of individual elements can also vary. For instance, center-to-center spacing of individual structures can be between about 50 nanometers and about 1 micrometer, for instance between about 100 nanometers and about 500 nanometers. For example, center-to-center spacing between structures can be on a nano-sized scale. For instance, when considering the spacing of nano-sized structures, the center-to-center spacing of the structures can be less than about 500 nanometers. This is not a requirement of a topography, however, and individual structures can be farther apart. The center-to-center spacing of structures can vary depending upon the size of the structures. For example, the ratio of the average of the cross-sectional dimensions of two adjacent structures to the center-to-center spacing between those two structures can be between about 1:1 (e.g., touching) and about 1:4, between about 1:1.5 and about 1:3.5, or between about 1:2 and about 1:3. For instance, the center to center spacing can be approximately double the average of the cross-sectional dimensions of two adjacent structures. In one embodiment, two adjacent structures each having a cross-sectional dimension of about 200 nanometers can have a center-to-center spacing of about 400 nanometers. Thus, the ratio of the average of the diameters to the center-to-center spacing in this case is 1:2.

Structure spacing can be the same, i.e., equidistant, or can vary for structures in a pattern. For instance, the smallest structures of a pattern can be spaced apart by a first distance, and the spacing between these smallest structures and a larger structure of the pattern or between two larger structures of the pattern can be the same or different as this first distance.

For example, in the pattern of FIG. 2, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures can be equidistant from one another or any variation in distances. In one embodiment, different structures can be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, the aspect ratio of the nanostructures may fall within these ranges.

Figure 3:
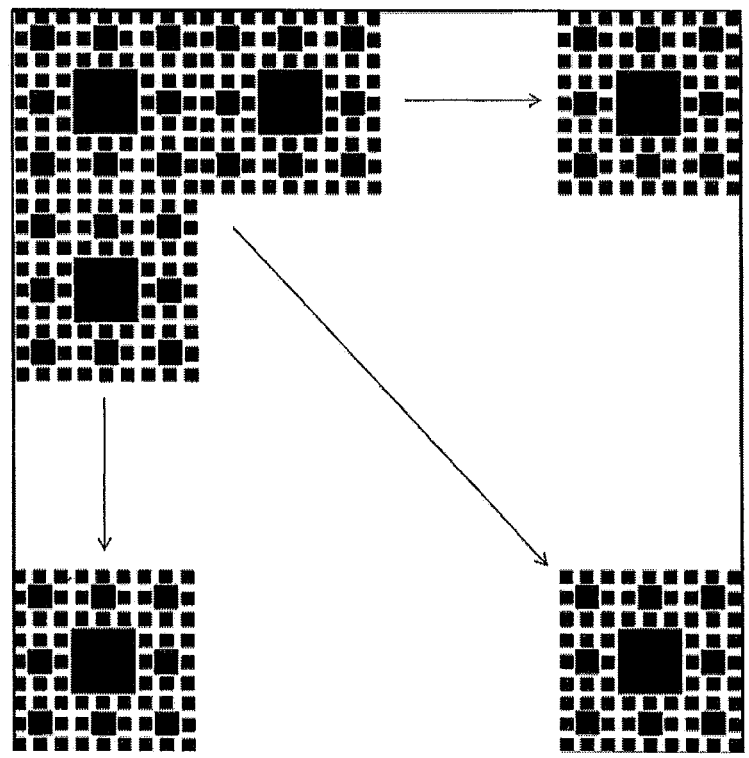
FIG. 3 illustrates a pattern including multiple iterations of the complex pattern of FIG. 2.

The device surface may include a single instance of a pattern, as shown in FIG. 2, or may include multiple iterations of the same or different patterns. For example, FIG. 3 illustrates a surface pattern including the pattern of FIG. 2 in multiple iterations over a surface.

The formation of nanotopography on a surface may increase the surface area without a corresponding increase in volume. Increase in the surface area to volume ratio is believed to improve the interaction of a surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins.

In general, the surface area to volume ratio of the device may be greater than about 10,000 $cm^{-1}$, greater than about 150,000 $cm^{-1}$, or greater than about 750,000 $cm^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, February, 1938, pp. 309-319), incorporated herein by reference. The BET surface area can be less than about 5 $m^2/g$, in one embodiment, for instance between about 0.1 $m^2/g$ and about 4.5 $m^2/g$, or between about 0.5 $m^2/g$ and about 3.5 $m^2/g$. Values for surface area and volume may also be estimated from the geometry of molds used to form a surface, according to standard geometric calculations. For example, the volume can be estimated according to the calculated volume for each pattern element and the total number of pattern elements in a given area, e.g., over the surface of a single microneedle.

For a device that defines a complex pattern nanotopography at a surface, the nanotopography may be characterized through determination of the fractal dimension of the pattern. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)},$$

where N(e) is the number of self-similar structures needed to cover the whole object when the object is reduced by 1/e in each spatial direction.

Figure 4:
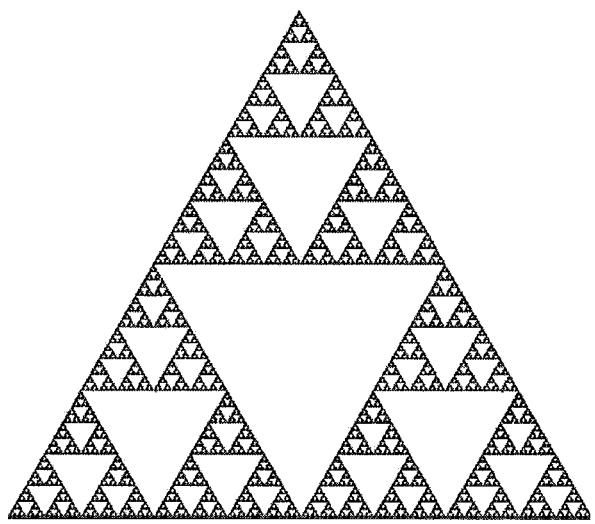
FIG. 4 illustrates a Sierpinski triangle fractal.

For example, when considering the two dimensional fractal known as the Sierpenski triangle illustrated in FIG. 4, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 2 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

Figure 5:
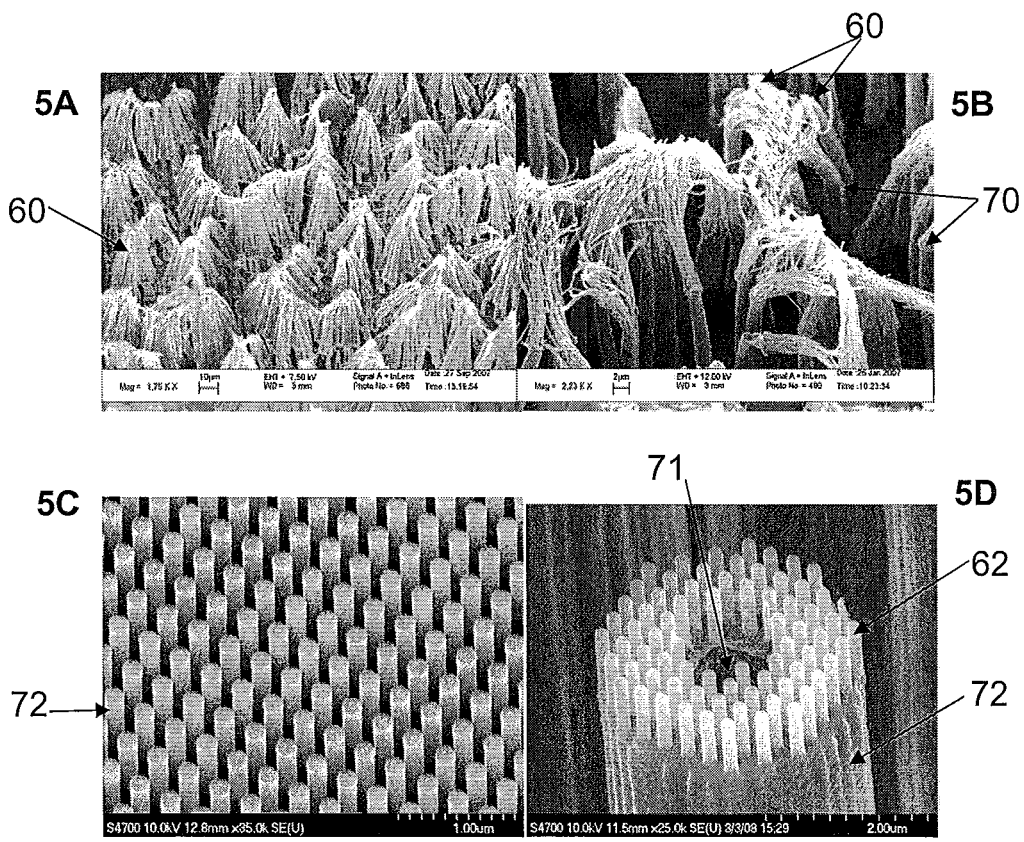
FIGS. 5A-5D illustrate complex fractal and fractal-like nanotopographies.

FIGS. 5A and 5B illustrate increasing magnification images of another example of a complex nanotopography. The nanotopography of FIGS. 5A and 5B includes an array of fibrous-like pillars 70 located on a substrate. At the distal end of each individual pillar, the pillar splits into multiple smaller fibers 60. At the distal end of each of these smaller fibers 60, each fiber splits again into multiple filaments (not visible in FIGS. 5A and 5B). Structures formed on a surface that have an aspect ratio greater than about 1 may be flexible, as are the structures illustrated in FIGS. 5A and 5B, or may be stiff.

FIGS. 5C and 5D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 5C and 5D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 6:
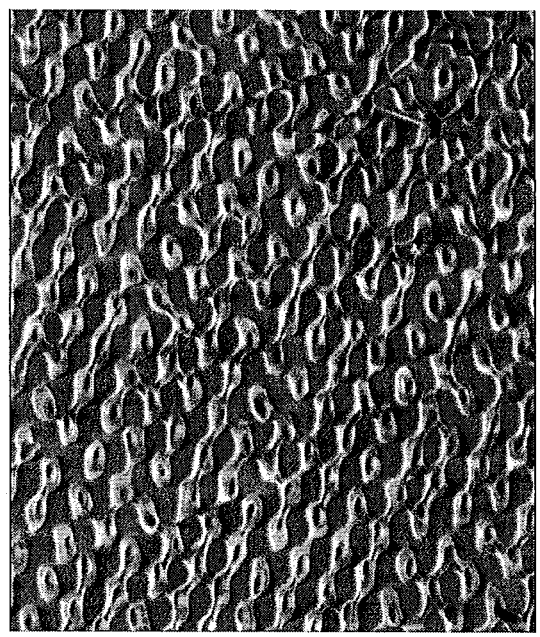
FIG. 6 illustrates another complex pattern that may be formed on a device surface.

FIG. 6 illustrates another pattern including nano-sized structures as may be formed on the device surface. As may be seen, in this embodiment, individual pattern structures may be formed at the same general size, but with different orientations and shapes from one another.

In addition to or alternative to those methods mentioned above, a surface may be characterized by other methods including, without limitation, surface roughness, elastic modulus, and surface energy.

Methods for determining the surface roughness are generally known in the art. For instance, an atomic force microscope process in contact or non-contact mode may be utilized according to standard practice to determine the surface roughness of a material. Surface roughness that may be utilized to characterize a device surface can include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers.

The device may be characterized by the elastic modulus of the nanopatterned surface, for instance by the change in elastic modulus upon the addition of a nanotopography to a surface. In general, the addition of a plurality of structures forming nanotopography on a surface can decrease the elastic modulus of a material, as the addition of nano-sized structures on a surface will lead to a reduction in continuity of the surface and a related change in surface area. As compared to a similar surface formed according to the same process and of the same materials, but for a pattern of nanotopography on the surface, the device surface including nanotopography thereon can exhibit a decrease in elastic modulus of between about 35% and about 99%, for instance between about 50% and about 99%, or between about 75% and about 80%. By way of example, the effective compression modulus of a nanopatterned surface can be less than about 50 MPa, or less than about 20 MPa. In one embodiment the effective compression modulus can be between about 0.2 MPa and about 50 MPa, between about 5 MPa and about 35 MPa, or between about 10 MPa and about 20 MPa. The effective shear modulus can be less than about 320 MPa, or less than about 220 MPa. For instance, the effective shear modulus can be between about 4 MPa and about 320 MPa, or between about 50 MPa and about 250 MPa, in one embodiment.

The device including nanotopography thereon may also exhibit an increase in surface energy as compared to a similar device surface that does not have a surface defining a pattern of nanotopography thereon. For instance, a surface including a nanotopography formed thereon can exhibit an increase in surface energy as compared to a similar surface of the same materials and formed according to the same methods, but for the inclusion of a pattern of nanotopography on a surface. For instance, the water contact angle of a surface including a nanotopography thereon can be greater than about 80°, greater than about 90°, greater than about 100°, or greater than about 110°. For example, the water contact angle of a surface can be between about 80° and about 150°, between about 90° and about 130°, or between about 100° and about 120°, in one embodiment.

Figures 7A, 7B:
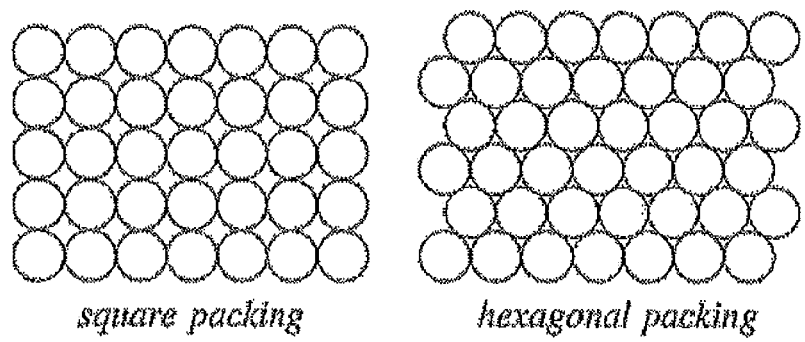
FIG. 7 illustrates exemplary packing densities as may be utilized for nano-sized structures as described herein including a square packing design (FIG. 7A), a hexagonal packing design (FIG. 7B), and a circle packing design (FIG. 7C).
Figure 7C:
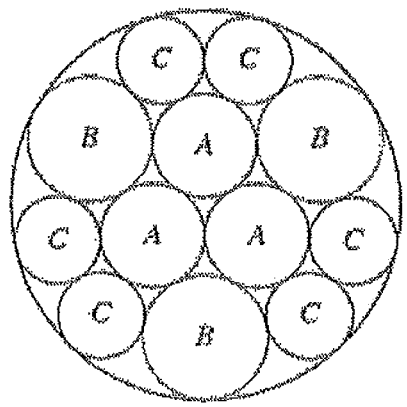

When forming nanostructures on the surface of the device, the packing density of the structures may be maximized. For instance, square packing (FIG. 7A), hexagonal packing (FIG. 7B), or some variation thereof may be utilized to pattern the elements on a substrate. When designing a pattern in which various sized elements of cross sectional areas A, B, and C are adjacent to one another on a substrate, circle packing as indicated in FIG. 7C may be utilized. Of course, variations in packing density and determination of associated alterations in characteristics of a surface are well within the abilities of one of skill in the art.

The device including a fabricated nanotopography on a surface of the device may be formed according to a single-step process. Alternatively, a multi-step process may be used, in which a pattern of nanostructures are fabricated on a pre-formed surface. For example, device may be first formed and then a random or non-random pattern of nanostructures may be fabricated on a surface of the formed device. In either the single-step or two-step process, structures may be fabricated on a surface or on a mold surface according to any suitable nanotopography fabrication method including, without limitation, nanoimprinting, injection molding, lithography, embossing molding, and so forth.

According to one embodiment, an implantable device including a fabricated nanotopography on a surface can be formed in a single-step process according to nanoimprint lithography methods utilizing ultra-high precision laser machining techniques, examples of which have been described by Hunt, et al. (U.S. Pat. No. 6,995,336) and Guo, et al. (U.S. Pat. No. 7,374,864), both of which are incorporated herein by reference. Nanoimprint lithography is a nano-scale lithography technique in which a hybrid mold is utilized which acts as both a nanoimprint lithography mold and a photolithography mask. A schematic of a nanoimprint lithography technique is illustrated in FIGS. 8A-8C. During fabrication, a hybrid mold 30 imprints into a substrate 32 via applied pressure to form features (e.g., a surface defining nanotopography) on a resist layer (FIG. 8A). In general, the surface of the substrate 32 may be heated prior to engagement with the mold 30 to a temperature above its glass transition temperature ($T_g$). While the hybrid mold 30 is engaged with the substrate 32, a flow of viscous polymer may be forced into the mold cavities to form features 34 (FIG. 8B). The mold and substrate may then be exposed to ultraviolet light. The hybrid mold is generally transmissive to UV radiation save for certain obstructed areas. Thus, the UV radiation passes through transmissive portions and into the resist layer. Pressure is maintained during cooling of the mold and substrate. The hybrid mold 30 is then removed from the cooled substrate 32 at a temperature below $T_g$ of the substrate and polymer (FIG. 10C).

Figure 10A:
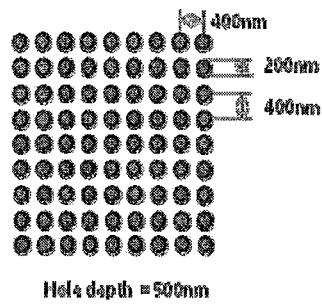
Figure 10A:
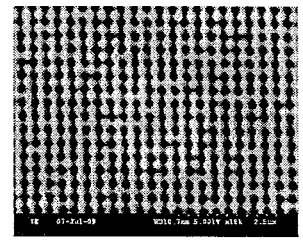
Figure 10B:
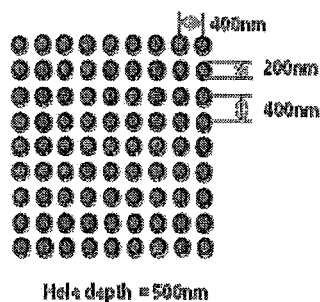
Figure 10B:
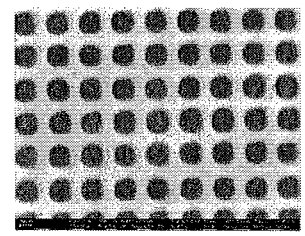
Figure 10C:
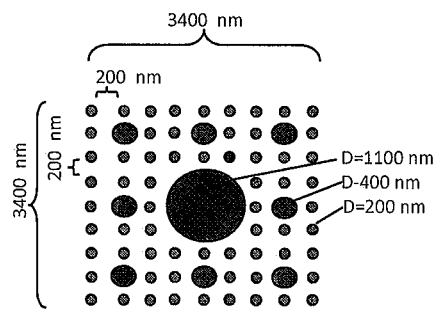
Figure 10C:
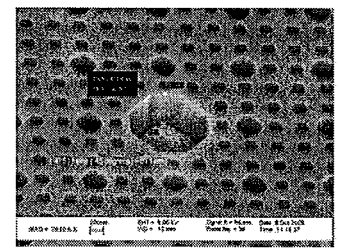

To facilitate the release of the nanoimprinted substrate 32 including fabricated features 34 from the mold 30, as depicted in FIG. 10C, it is advantageous to treat the mold 30 with a low energy coating to reduce the adhesion with the substrate 32, as a lower surface energy of the mold 30 and the resulting greater surface energy difference between the mold 30, substrate 32, and polymer may ease the release between the materials. By way of example, a silicon mold coating may be used such as trideca-(1,1,2,2-tetrahydro)-octytrichloro silane ($F_{13}$-TCS).

According to an exemplary two-step formation process, a film defining a plurality of nanostructures on a surface of the film may be formed, and the film may then be applied to a surface of a pre-formed implantable device. For instance, a pattern including the desired nanotopography may be formed on a mold according to photolithography techniques as described above, and this mold may be utilized to form a polymeric film defining the nanostructures thereon. Following formation, the film may be shaped as desired, e.g., cut, and applied to a surface of an implantable device, for instance by the application of heat and pressure to fuse the film to a surface of the device without deformation of the nanostructures of the film.

Structures may also be formed either on a mold or directly on a film or a device according to chemical addition processes. For instance, film deposition, sputtering, chemical vapor deposition (CVD); epitaxy (vapor phase, liquid phase, and molecular beam), electroplating, and so forth can be utilized for building structures on a surface.

Self-assembled monolayer processes as are known in the art can be utilized to form a pattern of structures on a surface. For instance, the ability of block copolymers to self-organize can be used to form a monolayer pattern on a surface. The pattern can then be used as a template for the growth of desired structures, e.g., colloids, according to the pattern of the monolayer.

By way of example, a two-dimensional, cross-linked polymer network can be produced from monomers with two or more reactive sites. Such cross-linked monolayers have been made using self-assembling monolayer (SAM) (e.g., a gold/alkyl thiol system) or Langmuir-Blodgett (LB) monolayer techniques (Ahmed et al., Thin Solid Films 187: 141-153 (1990)) as are known in the art. The monolayer can be crosslinked, which can lead to formation of a more structurally robust monolayer.

The monomers used to form a patterned monolayer can incorporate all the structural moieties necessary to affect the desired polymerization technique and/or monolayer formation technique, as well as to influence such properties as overall solubility, dissociation methods, and lithographic methods. A monomer can contain at least one, and more often at least two, reactive functional groups.

A molecule used to form an organic monolayer can include any of various organic functional groups interspersed with chains of methylene groups. For instance a molecule can be a long chain carbon structure containing methylene chains to facilitate packing. The packing between methylene groups can allow weak Van der Waals bonding to occur, enhancing the stability of the monolayer produced and counteracting the entropic penalties associated with forming an ordered phase. In addition, different terminal moieties, such as hydrogen-bonding moieties may be present at one terminus of the molecules, in order to allow growth of structures on the formed monolayer, in which case the polymerizable chemical moieties can be placed in the middle of the chain or at the opposite terminus. Any suitable molecular recognition chemistry can be used in forming the assembly. For instance, structures can be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule can be utilized to form the template. This additional molecule can have appropriate functionality at one of its termini in order to form a SAM. For example, on a gold surface, a terminal thiol can be included. There are a wide variety of organic molecules that may be employed to effect replication. Topochemically polymerizable moieties, such as dienes and diacetylenes, are particularly desirable as the polymerizing components. These can be interspersed with variable lengths of methylene linkers.

For an LB monolayer, only one monomer molecule is needed because the molecular recognition moiety can also serve as the polar functional group for LB formation purposes. Lithography can be carried out on a LB monolayer transferred to a substrate, or directly in the trough. For example, an LB monolayer of diacetylene monomers can be patterned by UV exposure through a mask or by electron beam patterning.

Monolayer formation can be facilitated by utilizing molecules that undergo a topochemical polymerization in the monolayer phase. By exposing the assembling film to a polymerization catalyst, the film can be grown in situ, and changed from a dynamic molecular assembly to a more robust polymerized assembly.

Any of the techniques known in the art for monolayer patterning may be used for patterning of the monolayer. Techniques useful in patterning a monolayer include, but are not limited to, photolithography, e-beam techniques, focused ion-beam techniques, and soft lithography. Various protection schemes such as photoresist can be used for a SAM-based system. Likewise, block copolymer patterns can be formed on gold and selectively etched to form patterns. For a two-component system, patterning can also be achieved with readily available techniques.

Soft lithography techniques can be utilized to pattern the monolayer in which ultraviolet light and a mask can be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer can be achieved by various growth mechanisms, such as through appropriate reduction chemistry of a metal salts and the use of seed or template-mediated nucleation. Using the recognition elements on the monolayer, inorganic growth can be catalyzed at this interface by a variety of methods. For instance inorganic compounds in the form of colloids bearing the shape of the patterned organic monolayer can be formed. For instance calcium carbonate or silica structures can be templated by various carbonyl functionalities such as carboxylic acids and amides. By controlling the crystal growth conditions, it is possible to control the thickness and crystal morphology of the mineral growth. Titanium dioxide can also be templated.

Templated electroless plating techniques can be used to synthesize metals using existing organic functional groups. In particular, by chelating metal atoms to the carbonyl moieties of the organic pattern, electroless metal deposition can be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art can be utilized, for example a method as described in U.S. Pat. No. 7,189,435 Tuominen, et al., which is incorporated herein by reference, can be utilized. According to this method, a conducting or semiconducting substrate (for example, a metal, such as gold) can be coated with a block copolymer film (for example, a block copolymer of methylmethacrylate and styrene), where one component of the copolymer forms nanoscopic cylinders in a matrix of another component of the copolymer. A conducting layer can then be placed on top of the copolymer to form a composite structure. Upon vertically orientation of the composite structure, some of the first component can be removed, for instance by exposure to UV radiation, an electron beam, or ozone, degradation, or the like to form nanoscopic pores in that region of the second component.

In another embodiment, described in U.S. Pat. No. 6,926,953 to Nealey, et al., incorporated herein by reference, copolymer structures can be formed by exposing a substrate with an imaging layer thereon, for instance an alkylsiloxane or an octadecyltrichlorosilane self assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) can then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nanometers or less.

The surface of an implantable delivery device can be further functionalized for improved interaction with tissues or individual cells during use. For instance, one or more biomolecules such as polynucleotides, polypeptides, entire proteins, polysaccharides, and the like can be bound to a device at the surface defining a nanotopography thereon, at a different surface of the device, or at both.

In some embodiments, a surface of a device can already contain suitable reactivity such that additional desired functionality may spontaneously attach to the surface with no pretreatment of the surface necessary. However, in other embodiments, pretreatment of the surface prior to attachment of the desired compound may be carried out. For instance, reactivity of a surface may be increased through addition or creation of amine, carboxylic acid, hydroxy, aldehyde, thiol, or ester groups on the surface. In one representative embodiment, a surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of an implantable delivery device can include ECM proteins such as laminins, tropoelastin or elastin, Tropocollagen or collagen, fibronectin, and the like. Short polypeptide fragments can be bound to the surface of a patterned device such as an RGD sequence, which is part of the recognition sequence of integrin binding to many ECM proteins. Thus, functionalization of a microneedle surface with RGD can encourage interaction of the device with ECM proteins and further limit foreign body response to the device during use.

The implantable delivery device may be in a form that may include various features. For example, the device may include a reservoir, e.g., a vessel, a porous matrix, etc., as discussed above that may store and agent and provide the agent for delivery. A reservoir may include a channel for delivery of a bioactive agent or may include a larger opening, for instance in the form of a notch formed at a device surface, which may contain the bioactive agent in a highly viscous composition, such as a gel. For instance, the device may include a hollow, or multiple pores that may carry one or more agents for delivery. The agent may be released from the device via degradation of a composition that carries the bioactive agent, via degradation of a portion or the entire device or via diffusion of the agent from the device, for instance via channels as discussed above.

For example, FIGS. 9A and 9B schematically illustrate a delivery device 110. Delivery device 110 can be utilized as a drug delivery patch alone, for instance in delivery of an active agent to an organ, or can additionally be utilized to provide structural support to a tissue. For instance, delivery device 110 can be applied to a blood vessel as a perivascular device, e.g., an aortic patch. Delivery device 110 can be utilized as a support structure such as a hernia patch, a bladder sling, or the like. In one embodiment, a delivery device 10 can be utilized to wrap a target, for instance an entire organ or a portion of an organ, a nerve bundle, a tumor, and the like. For example, cancerous tissue, such as a cancerous organ or individual targeted tissue can be wrapped so as to encircle one or more cancerous tumors in the tissue (or encircle the tumors as completely as possible, given the local architecture). The delivery device can then provide the eluted biologically active agent to the targeted tissue in a more complete fashion.

Device 110 is generally flexible and can be formed of any suitable material, as discussed previously for application to the external surface of an organ or a blood vessel, e.g., the aorta. At a surface 112 of device 110, a series of grooves 114 have been formed that can contain a composition including a bioactive agent.

FIG. 9B illustrates a section of the surface 112 of device 110. As can be seen grooves 114 have been formed in the surface 112. In this embodiment, the grooves 114 have a triangular cross sectional shape, but this is not a requirement, and any cross sectional shape as is known in the art may be utilized. The formation of a series of grooves 114 in the surface 112 or in the surface of a mold utilized to form the surface 112 can be carried out according to any standard microfabrication technique including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation). Surface 112 also includes a nanotopography 116 on the surface in those areas between the grooves 114. During use, the nanotopography can contact the tissue surface, e.g., the vessel wall in the case of a perivascular patch, and the bioactive agent loaded in to grooves 114, for instance in the form of a gel, can be delivered to the vessel, e.g., to the vessel wall or through the vessel wall and to the circulatory system.

The bioactive agent can be contained within or on the implantable delivery device according to any containment methodology as is known in the art. For example, in addition to containment within a reservoir and within surface grooves as discussed above, a bioactive agent can be coated on a device, or can be contained within or on a portion of a device, for instance within a biodegradable fiber or section of a device, and can be released over time as the device, or the portion thereof, degrades.

There is no particular limitation to bioactive agents as may be delivered by use of the implantable delivery devices.

Bioactive agents can encompass natural or synthetic agents, small molecule agents, and so forth. In one embodiment, methods may be utilized for delivery of high molecular weight bioactive agents (e.g., non-proteinaceous synthetic or natural bioactive agents defining a molecular weight greater than about 400 Da, greater than about 10 kDa, greater than about 20 kDa, or greater than about 100 kDa, e.g., about 150 kDa).

In one particular example, a bioactive agent can be a high molecular weight protein therapeutic. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. By way of example, a protein therapeutic having a molecular weight of greater than about 100 kDa, or greater than about 125 kDa, for instance from about 125 kDa to about 200 kDa, or from about 150 kDa to about 200 kDa, can be delivered by use of an implantable delivery device.

Agents may include proteinaceous agents such as immunoglobulins (e.g., IgG, IgM, IgA, IgE), TNF-α, antiviral medications, and so forth; polynucleotide agents including plasmids, siRNA, RNAi, nucleoside anticancer drugs, and so forth; and small molecule agents such as alkaloids, glycosides, phenols, and so forth. Agents may include anti-infection agents, hormones, drugs that regulate cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dopamine agonists and antagonists, enkephalins and other opioid peptides, growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, interferons, interleukins, leutenizing hormone, leutenizing hormone releasing hormone and analogs, monoclonal or polyclonal antibodies, muscle relaxants, narcotic analgesics, non-steroid anti-inflammatory agents, oligosaccharides, parathyroid hormone and analogs, parathyroid hormone antagonists, prostaglandin antagonists, prostaglandins, sedatives, serotonin agonists and antagonists, sexual hypofunction agents, tissue plasminogen activators, tranquilizers, vasodilators, major diagnostics such as tuberculin and other hypersensitivity agents as described in U.S. Pat. No. 6,569,143, the entire content of which is incorporated herein by reference. Vaccine formulations may include an antigen or antigenic composition capable of eliciting an immune response against a human pathogen or from other viral pathogens.

A composition may include one or more bioactive agents in conjunction with other components as are generally known in the art. For instance, a composition can include one or more pharmaceutically acceptable excipients. As utilized herein, the term "excipient" generally refers to any substance, not itself a bioactive agent, used in conjunction with the bioactive agent(s) delivered to a subject to improve one of more characteristics, such as its handling or storage properties or to permit or facilitate formation of a dose unit of the composition. Excipients include, by way of illustration and not limitation, solvents (e.g., lower alcohol, such as ethanol or isopropanol; or water), thickening agents, wetting agents, lubricants, substances added to mask or counteract a disagreeable odor or flavor, fragrances, adjuvants, and substances added to improve appearance or texture of the composition or delivery device. Any such excipients can be used in any amounts as are generally known.

Thickening agents (also referred to herein as gelling agents) may include anionic polymers such as polyacrylic acid (Carbopol® by Noveon, Inc., Cleveland, Ohio), carboxypolymethylene, carboxymethylcellulose and the like, including derivatives of Carbopol® polymers, such as Carbopol® Ultrez 10, Carbopol® 940, Carbopol® 941, Carbopol® 954, Carbopol® 980, Carbopol® 981, Carbopol® ETD 2001, Carbopol® EZ-2 and Carbopol® EZ-3, and other polymers such as Pemulen® polymeric emulsifiers, and Noveon® polycarbophils. Thickening agents, when present, can generally be present in a total amount by weight of from about 0.1% to about 15%, from about 0.25% to about 10%, or from about 0.5% to about 5%.

Additional thickening agents, enhancers and adjuvants may generally be found in Remington's The Science and Practice of Pharmacy as well as the Handbook f Pharmaceutical Excipients, Arthur H. Kibbe ed. 2000.

One or more neutralizing agents can be present to assist in forming a gel. Suitable neutralizing agents include sodium hydroxide (e.g., as an aqueous mixture), potassium hydroxide (e.g., as an aqueous mixture), ammonium hydroxide (e.g., as an aqueous mixture), triethanolamine, tromethamine (2-amino 2-hydroxymethyl-1,3 propanediol), aminomethyl propanol (AMP), tetrahydroxypropyl ethylene diamine, diisopropanolamine, Ethomeen C-25 (Armac Industrial Division), Di-2 (ethylhexyl) amine (BASF-Wyandotte Corp., Intermediate Chemicals Division), triamylamine, Jeffamine D-1000 (Jefferson Chemical Co.), b-Dimethylaminopropionitrite (American Cyanamid Co.), Armeen CD (Armac Industrial Division), Alamine 7D (Henkel Corporation), dodecylamine and morpholine. The neutralizing agent can be present in an amount sufficient to form a gel which is suitable for contact with the skin of a mammal, e.g., up to about 10% by weight of the composition, for example between about 0.1% and about 5% by weight of the composition.

A composition may include one or more pharmaceutically acceptable wetting agents (also referred to as surfactants) as excipients. Non-limiting examples of surfactants can include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of 101), propylene glycol fatty acid esters, for example propylene glycol laurate (e.g., Lauroglycol™ of Gattefosse), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof.

One or more wetting agents, when present, generally constitute in total from about 0.25% to about 15%, from about 0.4% to about 10%, or from about 0.5% to about 5%, of the total weight of the composition.

A composition may include one or more pharmaceutically acceptable lubricants (including anti-adherents and/or glidants) as excipients. Suitable lubricants include, without limitation, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, when, can generally constitute from about 0.1% to about 10%, from about 0.2% to about 8%, or from about 0.25% to about 5%, of the total weight of the composition.

A composition may include one or more antimicrobial preservative. Illustrative anti-microbial preservatives include, without limitation, benzoic acid, phenolic acid, sorbic acids, alcohols, benzethonium chloride, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, propylparaben, sodium propionate, or thimerosal. One or more anti-microbial preservatives, when present, can generally be present in a total amount of from about 0.1% to about 5%, from about 0.2% to about 3%, or from about 0.3% to about 2%, by weight of the composition.

A composition may include one or more emulsifying agents. As utilized herein, the term "emulsifying agent" generally refers to an agent capable of lowering surface tension between a non-polar and polar phase and includes compounds defined as "self-emulsifying" agents. Suitable emulsifying agents can come from any class of pharmaceutically acceptable emulsifying agents including carbohydrates, proteins, high molecular weight alcohols, wetting agents, waxes and finely divided solids. One or more emulsifying agents, when present, can be present in a composition in a total amount of from about 1% to about 15%, from about 1% to about 12%, from about 1% to about 10%, or from about 1% to about 5% by weight of the composition.

A composition including a bioactive agent can be a sustained release composition as is generally known in the art. Such compositions can be desirable, for instance, in situations where long term delivery of the agents to a particular organ or vascular location is desired. According to this particular embodiment, a bioactive agent can be incorporated in a sustained-release matrix that can include degradable materials, usually polymers, which are degradable by enzymatic or acid/base hydrolysis or by dissolution. Once the implantable device is located at or near the target tissue, e.g., inserted into the body, for instance in the form of a patch or a stent such as those further described herein, such a matrix can be acted upon by enzymes and body fluids. The sustained-release matrix can be chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Possible biodegradable polymers and their use are described, for example, in detail in Brem et al. (1991, *J. Neurosurg.* 74:441-6), which is hereby incorporated by reference in its entirety.

The composition can be prepared by any technique known to a person of ordinary skill in the art of pharmacy, pharmaceutics, drug delivery, pharmacokinetics, medicine or other related discipline that comprises admixing one or more excipients with a therapeutic agent to form a composition, drug delivery system or component thereof.

The subject matter of this disclosure may be better understood with reference to the Examples, provided below.

Example 1

Several different molds were prepared using photolithography techniques similar to those employed in the design and manufacture of electrical circuits. Individual process steps are generally known in the art and have been described Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:
Beam current=11 nA
Acceleration voltage=100 kV
Shot pitch=14 nm
Dose=260 µC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm) He, 22 sccm $CF_4$, 20 sccm $C_4F_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm $Cl_2$ and 5 sccm Ar at 5 mTorr, 600 W coil, 50 W RIE and a DC Bias of 96-102 V. The silicon etch depth was 500 nanometers.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nanometers at 1.8 W/cm$^2$. A UV filter of 250-400 nanometers was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Figure 10D:
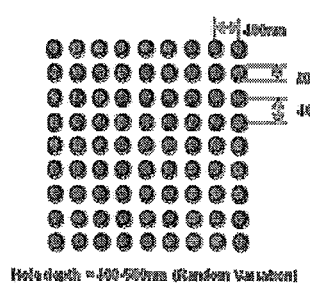
Figure 10D:
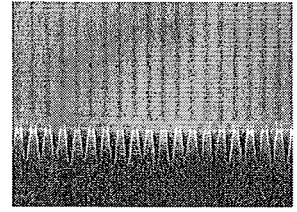
Figure 12A:
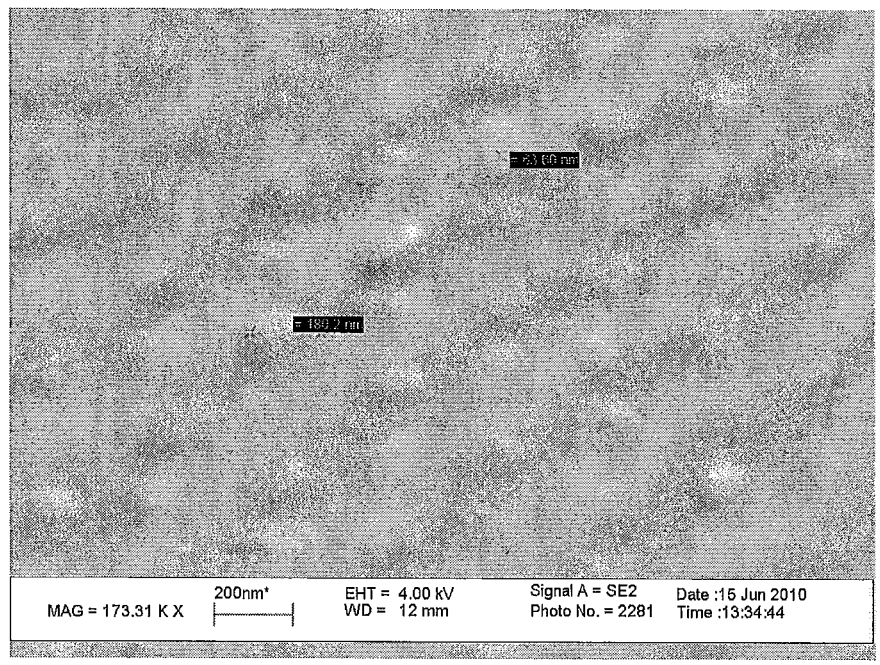
FIGS. 12A and 12B are two SEM of a film including another nanopatterned surface.
Figure 12B:
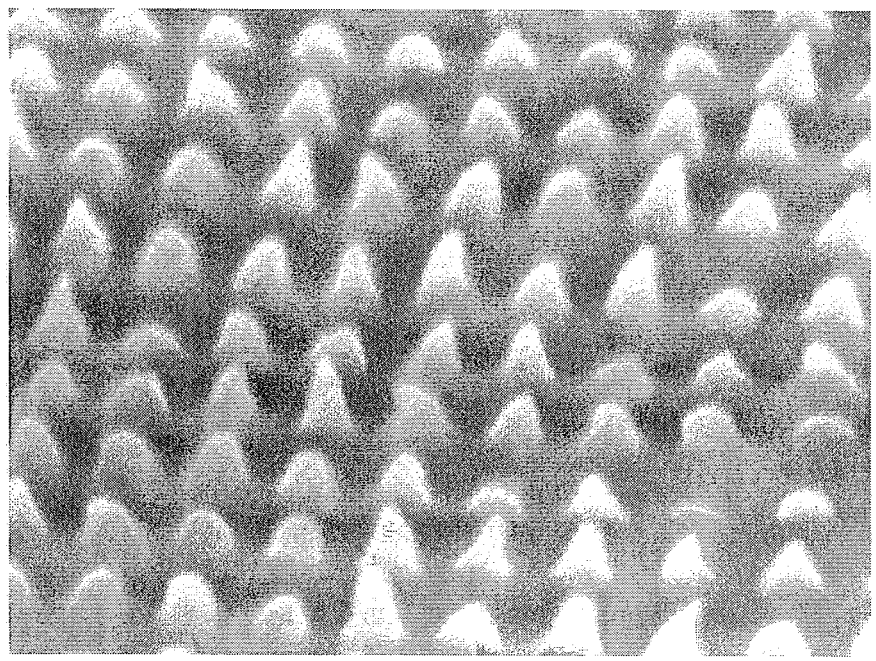
Figure 13:
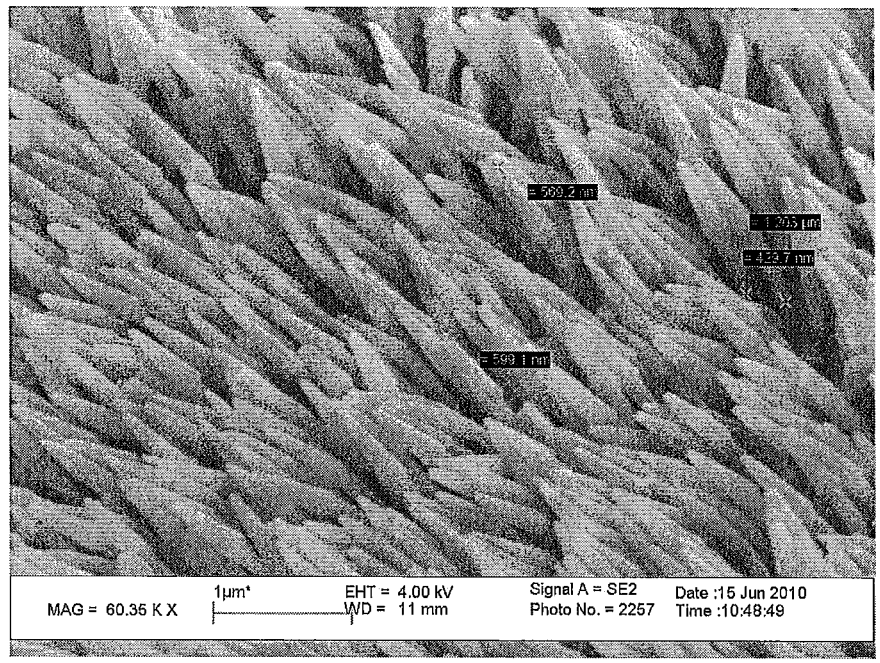
FIG. 13 is an SEM of a film including another nanopatterned surface.
Figure 14:
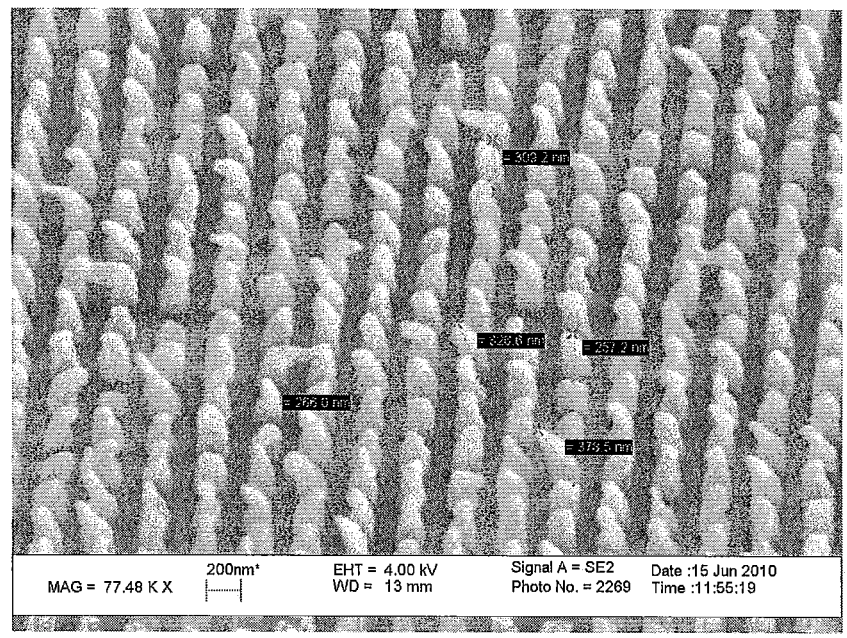
FIG. 14 is an SEM of a film including another nanopatterned surface.
Figure 15:
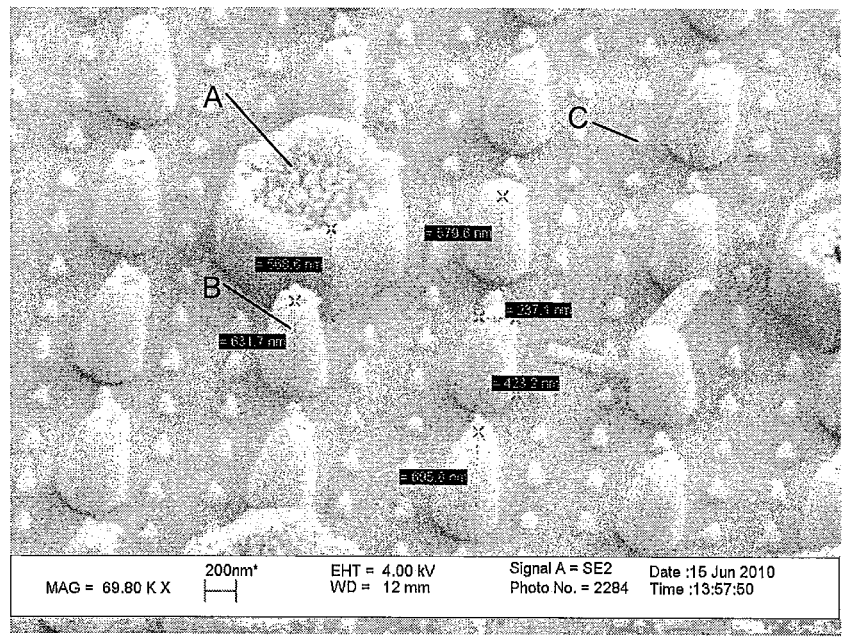
FIG. 15 is an SEM of a film including another nanopatterned surface.
Figure 16:
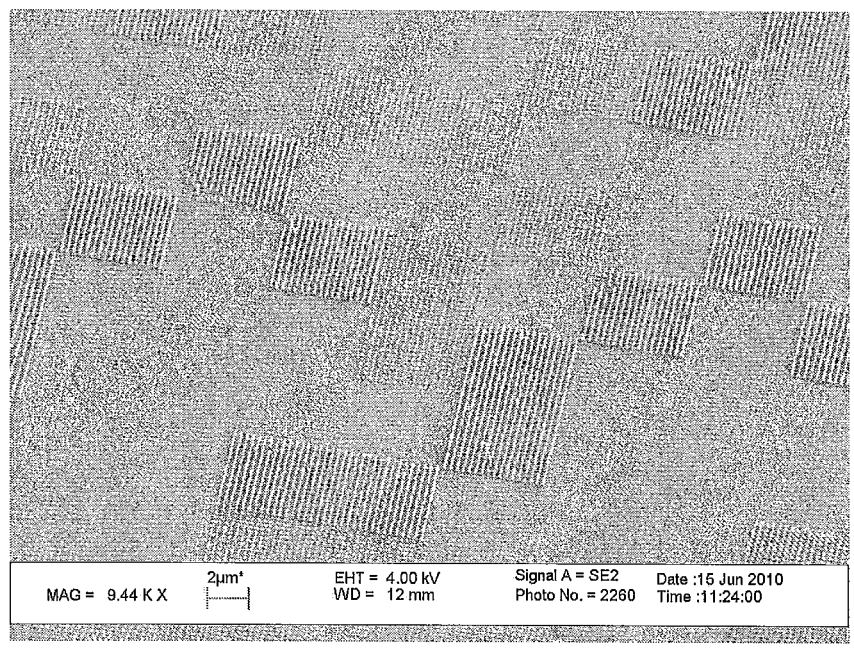
FIG. 16 is an SEM of a film including another nanopatterned surface.
Figure 17:
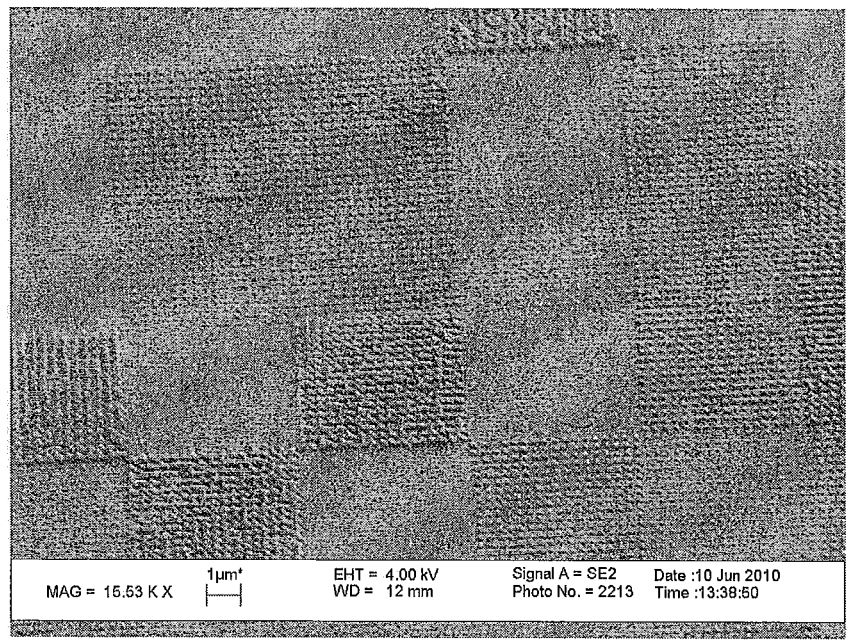
FIG. 17 is an SEM of a film including another nanopatterned surface.
Figure 18:
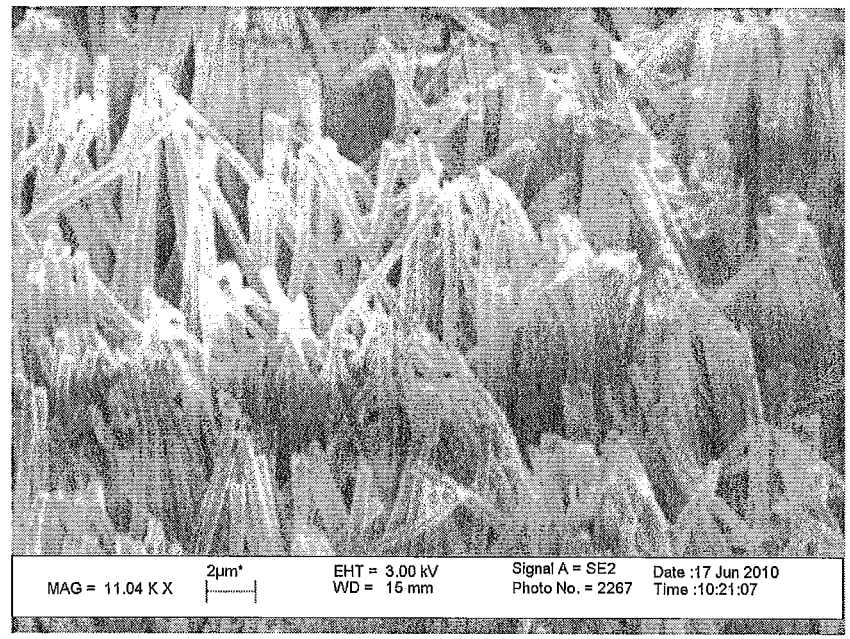
FIG. 18 is an SEM of a film including another nanopatterned surface.
Figure 19:
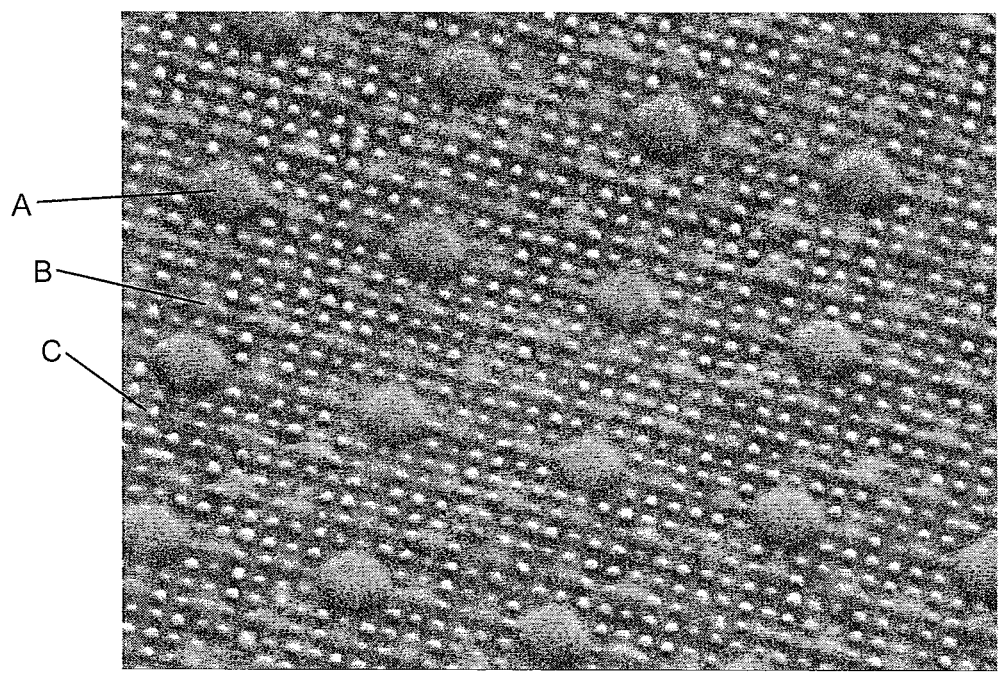
FIG. 19 is an SEM of a film including another nanopatterned surface.

Several different nanotopography patterns were formed, schematic representations of which are illustrated in FIGS. 10A-10D. The nanotopography pattern illustrated in FIG. 10E was a surface of a flat substrate purchased from NTT Advanced Technology of Tokyo, Japan. The patterns were designated DN1 (FIG. 10A), DN2 (FIG. 10B), DN3 (FIG. 10C), DN4 (FIG. 10D) and NTTAT2 (FIG. 10E). SEM images of the molds are shown in FIGS. 10A, 10B, and 10C, and images of the films are shown in FIGS. 10D and 10E. FIG. 6 illustrates a nanopatterned film formed by use of the mold of FIG. 10A (DN1). In this particular film, the polymer features were drawn by temperature variation as previously discussed. The surface roughness of the pattern of FIG. 10E was found to be 34 nanometers.

The pattern illustrated in FIGS. 5C and 5D was also formed according to this nanoimprinting process. This pattern included the pillars 72 and pillars 62, as illustrated. Larger pillars 72 were formed with a 3.5 micrometer (μm) diameter and 30 μm heights with center-to-center spacing of 6.8 μm. Pillars 62 were 500 nanometers in height and 200 nanometers in diameter and a center-to-center spacing of 250 nanometers.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

Example 2

Films were formed as described above in Example 1 including various different patterns and formed of either polystyrene (PS) or polypropylene (PP). The underlying substrate varied in thickness. Patterns utilized were DN2, DN3, or DN4 utilizing formation processes as described in Example 1. The pattern molds were varied with regard to hole depth and feature spacing to form a variety of differently-sized features having the designated patterns. Sample no. 8 (designated BB1) was formed by use of a 0.6 μm millipore polycarbonate filter as a mold. A 25 μm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are shown in FIGS. 11-19 and the characteristics of the formed films are summarized in Table 3, below.

TABLE 3

| Sample No. | Fig. | Pattern | Material | Film thickness (μm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 11 | DN3 | PS | 75 | A | 1100 nm | 520 nm | 0.47 | 150 | 2.0 | 100° |
|  |  |  |  |  | B | 400 nm | 560 nm | 1.4 |  |  |  |
|  |  |  |  |  | C | 200 nm | 680 nm | 3.4 |  |  |  |
| 2 | 22A, 22B | DN2 | PP | 5.0 | n/a | 200 nm | 100 nm | 0.5 | 16 | 2.15 | 91° |
| 3 | 13 | DN2 | PS | 75 | n/a | 200 nm | 1.0 μm | 5 | 64 | 2.2 | 110° |
| 4 | 14 | DN2 | PP | 25.4 | n/a | 200 nm | 300 nm | 1.5 | 38 | 1.94 | 118° |
| 5 | 15 | DN3 | PS | 75 | A | 1100 nm | 570 nm | 0.52 | 21.1 | 1.98 | 100° |
|  |  |  |  |  | B | 400 nm | 635 nm | 1.6 |  |  |  |
|  |  |  |  |  | C | 200 nm | — | — |  |  |  |
| 6 | 16 | DN4 | PS | 75 | n/a | 200 nm | — | — | 30.6 | 2.04 | 80° |
| 7 | 17 | DN4 | PP | 25.4 | n/a | 200 nm | — | — | 21.4 | 2.07 | 112° |
| 8 | 18 | BB1 | PP | 25.4 | n/a | 600 nm | 18 μm | 30 | 820 | 2.17 | 110° |
| 9 | 19 | DN3 | PP | 5 | A | 1100 nm | 165 nm | 0.15 | 50 | 2.13 | — |
|  |  |  |  |  | B | 400 nm | 80 nm | 0.2 |  |  |  |
|  |  |  |  |  | C | 200 nm | 34 nm | 0.17 |  |  |  |

[1]Pattern Features as shown on the figures.
[2]Cross sectional dimension values were derived from the mold and equated as an approximation of the maximum dimension of the structures, although it should be understood that the actual dimension of any given individual structure may vary slightly as may be seen in the figures.
[3]Feature heights are provided as the average of several individually determined feature heights.

For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from μMasch. The cantilever had a resonant frequency of 170 kHz, a spring constant of 40 N/m, a length of 230±5 μm, a width of 40±3 µm, and a thickness of 7.0±0.5 µm. The probe tip was an n-type phosphorous-doped silicon probe, with a typical probe tip radius of 10 nanometers, a full tip cone angle of 40°, a total tip height of 20-25 µm, and a bulk resistivity 0.01-0.05 ohm-cm.

The surface roughness value given in Table 3 is the arithmetical mean height of the surface area roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

The fractal dimension can also be evaluated from 2D Fourier spectra by application of the Log function. If the surface is fractal the Log graph should be highly linear, with at negative slope (see, e.g., Fractal Surfaces, John C. Russ, Springer-Verlag New York, LLC, July, 2008).

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A fully implantable delivery device configured to deliver a bioactive agent to a subject, the device comprising:
   the bioactive agent;
   a wall having a surface;
   a plurality of nanostructures extending from the surface of the wall, at least a portion of the nanostructures having a cross-sectional dimension of greater than about 5 nanometers and less than about 500 nanometers, and a height of greater than about 5 nanometers to less than about 1 micrometer, and wherein at least a portion of the nanostructures have a center-to-center spacing of greater than about 50 nanometers to less than about 1 micrometer, and
   a plurality of microstructures extending from the surface of the wall, at least a portion of the microstructures having a cross-sectional dimension of greater than about 500 nanometers and less than about 10 micrometers and a height of from about 20 nanometers to about 1 micrometer, wherein the cross-sectional dimension of each nanostructure of the plurality of nanostructures is smaller than the cross-sectional dimension of each microstructure of the plurality of microstructures;
   wherein the plurality of nanostructures and plurality of microstructures are arranged in a fractal dimension of greater than about 1; and
   wherein the surface containing the plurality of nanostructures and plurality of microstructures has an average surface roughness, as determined by an arithmetical mean height of a surface area roughness parameter as defined by ISO 25178, between about 10 nanometers and about 200 nanometers.

2. The fully implantable delivery device according to claim 1, wherein the bioactive agent is a component of a composition, the composition further comprising one or more pharmaceutically acceptable excipients.

3. A fully implantable delivery device configured to deliver a bioactive agent to a subject, the device comprising:
   the bioactive agent;
   a wall having a surface;
   a plurality of nanostructures extending from the surface of the wall, at least a portion of the nanostructures having a cross-sectional dimension of greater than about 5 nanometers and less than about 300 nanometers, and a height of greater than about 5 nanometers to less than about 1 micrometer, and wherein at least a portion of the nanostructures have a center-to-center spacing of greater than about 50 nanometers to less than about 1 micrometer, and
   a plurality of microstructures extending from the surface of the wall, at least a portion of the microstructures having a cross-sectional dimension of greater than about 500 nanometers and less than about 10 micrometers and a height of from about 20 nanometers to about 1 micrometer, wherein the cross-sectional dimension of each nanostructure of the plurality of nanostructures is smaller than the cross-sectional dimension of each microstructure of the plurality of microstructures;
   wherein the plurality of nanostructures and plurality of microstructures are arranged in a fractal dimension of greater than about 1;
   wherein the surface containing the plurality of nanostructures and plurality of microstructures has an average surface roughness, as determined by an arithmetical mean height of a surface area roughness parameter as defined by ISO 25178, between about 10 nanometers and about 200 nanometers.

4. The fully implantable delivery device according to claim 1, wherein the plurality of nanostructures comprises first nanostructures and second nanostructures, and wherein the second nanostructures have a cross-sectional dimension less than the cross-sectional dimension of the microstructures and greater than the cross-sectional dimension of the first nanostructures.

5. The fully implantable delivery device according to claim 1, wherein the surface containing the plurality of nanostructures has an effective shear modulus between about 4 MPa and about 320 MPa.

6. A fully implantable delivery device for delivery of a bioactive agent to a subject, the device comprising:
   a wall having a surface;
   a plurality of nanostructures extending from the surface of the wall, at least a portion of the nanostructures having a cross-sectional dimension of greater than about 5 nanometers and less than about 500 nanometers, and a height of greater than about 5 nanometers to less than about 1 micrometer, and wherein at least a portion of the nanostructures have a center-to-center spacing of greater than about 50 nanometers to less than about 1 micrometer,
   a plurality of microstructures extending from the surface of the wall, at least a portion of the microstructures having a cross-sectional dimension of greater than about 500 nanometers and less than about 10 micrometers and a height of from about 20 nanometers to about 1 micrometer; and
   a reservoir defined by the wall and containing the bioactive agent suitable for delivering to the subject using the implantable delivery device,
   wherein the entire implantable delivery device is suitable for implanting in the subject and configured to interact with tissue near a site of implantation within the subject;

wherein the plurality of nanostructures and plurality of microstructures are arranged in a fractal dimension of greater than about 1; and wherein the surface containing the plurality of nanostructures and plurality of microstructures has an average surface roughness, as determined by an arithmetical mean height of a surface area roughness parameter as defined by ISO 25178, between about 10 nanometers and about 200 nanometers.

7. The fully implantable delivery device according to claim 1, the device comprising a groove on a surface of the device, wherein the bioactive agent is contained within the groove.

8. The fully implantable delivery device according to claim 1, wherein at least a portion of the nanostructures have an aspect ratio of from about 0.2 to about 5.

9. The fully implantable delivery device according to claim 1, wherein the bioactive agent is a component of a composition, the composition further comprising a sustained release matrix.

10. The fully implantable delivery device according to claim 1, wherein at least a portion of the nanostructures have a cross-sectional dimension of from about 100 to about 300 nanometers.

11. The fully implantable delivery device according to claim 1, wherein at least a portion of the nanostructures have approximately the same cross-sectional dimension.

12. The fully implantable delivery device according to claim 1, wherein a ratio of the cross-sectional dimension of two adjacent nanostructures to the center-to-center spacing between those the two nanostructures is between about 1:1 and about 1:4.

13. The fully implantable delivery device according to claim 1, wherein at least a portion of the nanostructures have an equidistant spacing.

14. The fully implantable delivery device according to claim 1, wherein at least a portion of the nanostructures have a cross-sectional dimension of from about 20 to about 400 nanometers and at least a portion of the microstructures have a cross-sectional dimension of from about 600 nanometers to about 1.5 micrometers.

15. The fully implantable delivery device according to claim 1, wherein at least a portion of the microstructures have a height of from about 20 nanometers to about 1 micrometer.

16. The fully implantable delivery device according to claim 1, wherein at least a portion of the microstructures have an aspect ratio of from about 0.2 to about 5.

17. The fully implantable delivery device according to claim 1, wherein at least a portion of the nanostructures have an aspect ratio of from about 0.5 to about 3.5.

18. The fully implantable delivery device according to claim 1, wherein the cross-sectional dimension of the microstructures is greater than the height of the microstructures.

19. The fully implantable delivery device according to claim 18, wherein at least a portion of the microstructures have an aspect ratio of from about 0.15 to 1.

20. The fully implantable delivery device according to claim 1, wherein at least a portion of the nanostructures have a height greater than a cross-sectional dimension.

* * * * *